(12) United States Patent
Ueda

(10) Patent No.: US 9,795,280 B2
(45) Date of Patent: Oct. 24, 2017

(54) ENDOSCOPE SYSTEM HAVING CONNECTOR

(71) Applicant: FUJIFILM Corporation, Tokyo (JP)

(72) Inventor: Yoshihiro Ueda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 574 days.

(21) Appl. No.: 14/339,679

(22) Filed: Jul. 24, 2014

(65) Prior Publication Data

US 2015/0073214 A1    Mar. 12, 2015

(30) Foreign Application Priority Data

Sep. 6, 2013  (JP) .................................. 2013-185208

(51) Int. Cl.
*A61B 1/00* (2006.01)
*A61B 1/12* (2006.01)
*A61B 1/015* (2006.01)

(52) U.S. Cl.
CPC ...... *A61B 1/00128* (2013.01); *A61B 1/00119* (2013.01); *A61B 1/015* (2013.01); *A61B 1/121* (2013.01)

(58) Field of Classification Search
CPC ............ A61B 1/00112; A61B 1/00119; A61B 1/00121; A61B 1/00128
USPC ................................................ 600/132, 159
See application file for complete search history.

(56) References Cited

U.S. PATENT DOCUMENTS

| | | | | |
|---|---|---|---|---|
| 4,800,869 A * | 1/1989 | Nakajima | .......... | A61B 1/00068 600/158 |
| 5,971,917 A | 10/1999 | Komi et al. | | |
| 7,568,735 B2 | 8/2009 | Akiba | | |
| 8,454,498 B2 * | 6/2013 | Cushner | ................ | A61M 39/10 600/132 |

FOREIGN PATENT DOCUMENTS

| | | | |
|---|---|---|---|
| JP | 5-228105 | A | 9/1993 |
| JP | 8-112247 | A | 5/1996 |
| JP | 9-201328 | A | 8/1997 |
| JP | 10-234666 | A | 9/1998 |
| JP | 11-104076 | A | 4/1999 |
| JP | 2013-106711 | A | 4/1999 |
| JP | 3712820 | B2 | 11/2005 |
| JP | 2006-149556 | A | 6/2006 |
| JP | 4144444 | B2 | 9/2008 |
| JP | 2013-135843 | A | 7/2013 |

OTHER PUBLICATIONS

Japanese Office Action and English translation thereof, dated Aug. 24, 2016, for counterpart Japanese Application No. 2015-196652.

* cited by examiner

*Primary Examiner* — Matthew J Kasztejna
(74) *Attorney, Agent, or Firm* — Birch, Stewart, Kolasch & Birch, LLP

(57) ABSTRACT

An endoscope system includes an endoscope and a cleaning adapter or connector. The endoscope has a port device or end sleeve, to which the cleaning adapter is coupled. The cleaning adapter includes a connector housing and a coupling sleeve, which has a male tapered portion. The connector housing includes a female thread (fastening device) and a guide surface. The port device includes a flange and a male thread. The guide surface guides the port device by contacting the flange. Thus, a male tapered surface or tapered sealing surface is axially aligned with a female tapered surface or tapered bore surface. The male tapered surface tightly contacts the female tapered surface by threaded engagement between the male and female threads. Accordingly, air-tightness or liquid-tightness can be ensured even in use of a plurality of connectors couplable selectively for connecting a related apparatus.

15 Claims, 23 Drawing Sheets

ENDOSCOPE SYSTEM HAVING CONNECTOR

CROSS-REFERENCE TO RELATED APPLICATION

This application claims priority under 35 USC 119 from Japanese Patent Application No. 2013-185208, filed 6 Sep. 2013, the disclosure of which is incorporated by reference herein.

BACKGROUND OF THE INVENTION

1. Field of the Invention

The present invention relates to an endoscope system having a connector. More particularly, the present invention relates to an endoscope system in which an endoscope is connected by a connector with a related apparatus, and in which air-tightness or liquid-tightness can be ensured even in use of a plurality of connectors couplable selectively.

2. Description Related to the Prior Art

An endoscope is used widely in the medical field, and includes a fluid channel, such as a fluid supply channel for supplying air or water as fluid to a tip device of an elongated tube, and a suction channel for suction of fluid. An example of the endoscope has a balloon at the tip device of the elongated tube. A flow channel for inflating and deflating the balloon is provided in the endoscope. For those purposes, a fluid supply source is connected to the fluid supply channel, a suction apparatus is connected to the suction channel, and a balloon control apparatus is connected to the flow channel for supplying and drawing fluid. A port device or end sleeve is disposed at a proximal end of the fluid channel for connection of a related apparatus of those examples.

Connection of the fluid source apparatus or the related apparatus (suction apparatus) to the fluid channel of the endoscope requires a removable structure with respect to the port device of the fluid channel and also air-tightness or liquid-tightness. For example, JP-A 2006-149556 (corresponding to JP-B 4458258) and U.S. Pat. No. 5,971,917 (corresponding to JP-B 3712820) disclose seal packing positioned for sealing between the port device and a connector of the related apparatus, to press the seal packing to the port device.

JP-A 2006-149556 discloses a cleaning adapter or the connector for the endoscope. The connector includes a flow sleeve, the seal packing, a guide device of a housing, a slide mechanism and a coil spring. The flow sleeve is receivable in the port device of the endoscope. The seal packing seals the flow sleeve. The slide mechanism has the flow sleeve positioned stationarily, and is movable back and forth relative to the guide device. The coil spring is disposed between the slide mechanism and the guide device. The seal packing contacts an end face of the port device. Upon shifting the slide mechanism relative to the guide device, a flange of the port device is latched between the guide device and the flow sleeve. The coil spring presses the flow sleeve to tighten the contact of the seal packing with the port device. Also, U.S. Pat. No. 5,971,917 discloses the endoscope in which a male thread is formed with the port device. A female thread is formed with the connector, and helically engaged with the male thread to press the seal packing.

U.S. Pat. No. 7,568,735 (corresponding to JP-B 4144444), JP-A 9-201328 and JP-A 8-112247 discloses the endoscope and the connector in combination with the endoscope. A female tapered surface or tapered bore surface is defined inside the port device and has a predetermined taper angle. A male tapered surface or tapered sealing surface is formed at a tip of a coupling sleeve of the connector. The male tapered surface is tightly fitted on the female tapered surface by engaging the coupling sleeve with the inside of the port device, for maintaining air-tightness.

While the seal packing for sealing the port device of the endoscope is new, air-tightness and liquid-tightness are sufficient. However, degradation of the seal packing lowers tightness in the sealing with the port device, considerably to lose air-tightness and liquid-tightness. In view of this, a disposable type of the connector with the seal packing is useful for manipulation of entry of the elongated tube of the endoscope in a body cavity (gastrointestinal tract) for imaging, diagnosis and treatment of the body of the patient. The connector is connected to the related apparatus. In contrast with this, a reusable type of the connector is useful in combination with a syringe for cleaning, tube cleaning apparatus or the like for operation with durability with time. The reusable type does not include the seal packing but constructed for air-tightness and liquid-tightness.

Although the seal packing in the connector of JP-A 2006-149556 and U.S. Pat. No. 5,971,917 is effective in keeping air-tightness and liquid-tightness, mechanical construction is complicated, inclusive of the coil spring for pressing the flow sleeve, the slide mechanism for latching the flange of the port device, and the female thread for engagement with the port device. The connector cannot be disposable due to a considerably high manufacturing cost.

The construction of U.S. Pat. No. 7,568,735, JP-A 9-201328 and JP-A 8-112247 do not have the seal packing but have the female tapered surface and the male tapered surface fitted on each other to keep air-tightness and liquid-tightness in combination of the endoscope with the connector. However, there is no disclosure for precisely positioning the female tapered surface and the male tapered surface in the axial direction. Air-tightness or liquid-tightness may be insufficient assuming that the connector is used repeatedly with a tube cleaning apparatus or the like.

SUMMARY OF THE INVENTION

In view of the foregoing problems, an object of the present invention is to provide an endoscope system in which an endoscope is connected by a connector with a related apparatus, and in which air-tightness or liquid-tightness can be ensured even in use of a plurality of connectors couplable selectively.

In order to achieve the above and other objects and advantages of this invention, an endoscope system includes an endoscope and first and second connectors, the endoscope having an elongated tube for entry in a body cavity for imaging, a fluid channel, formed inside the elongated tube, for transferring fluid, and a port device, disposed on a proximal end side of the elongated tube, for communicating with the fluid channel, the first and second connectors being selectively coupled with the port device. In the endoscope system, (A) the port device includes a sleeve portion having an opening. A flange is formed to project radially from an outer surface of the sleeve portion. A first tapered portion is formed in the opening. (B) The first connector includes a flow sleeve for entry in the opening. A sealing structure seals an outer surface of the flow sleeve entered in the opening. There is an engaging device for engagement with the flange. (C) The second connector includes a coupling sleeve for entry in the opening. A second tapered portion is formed with the coupling sleeve, and tapered in compliance with the first tapered portion. A fastening device fastens with the port device. A pusher presses the second tapered portion to the first tapered portion upon fastening of the fastening device with the port device, to seal the first and second tapered portions.

In a preferred embodiment, the first tapered portion is a female tapered surface formed inside the port device, and the second tapered portion is a male tapered surface.

Preferably, at least a portion of the second connector having the second tapered portion is metallic.

Preferably, furthermore, a male thread is formed with the port device. The fastening device includes a female thread for threaded engagement with the male thread for fastening.

Preferably, the pusher is constituted by the female thread, and the second tapered portion is pressed to the first tapered portion according to threaded engagement of the female thread with the male thread.

Preferably, furthermore, a guide surface is disposed around the second tapered portion, for guiding the port device, to position the first tapered portion on the second tapered portion.

Preferably, the second connector includes a hole opening disposed so as to receive the port device. The female thread is disposed between the hole opening and the guide surface, and the male thread is disposed between the flange and the fluid channel.

Preferably, a size of the female thread in an axial direction is shorter than a distance from an upper end of the flange to the male thread in the axial direction.

Preferably, a difference between a size of the female thread in an axial direction and a distance from an upper end of the flange to the male thread in the axial direction is equal to or more than 1 mm and equal to or less than 3 mm.

In another preferred embodiment, the second connector includes a hole opening disposed so as to receive the port device. The guide surface is disposed between the hole opening and the female thread, and the male thread is disposed around the flange.

Preferably, furthermore, a guide projection is formed around the port device between the flange and the fluid channel, for guiding by contacting the guide surface.

In one preferred embodiment, the pusher includes a biasing device for biasing the second tapered portion toward the port device. The fastening device includes a shifting device movable between a latched position and a released position, the shifting device being engaged with a lower end of the flange, for fastening the second connector to the port device by latching the port device with the second tapered portion upon being set in the latched position, the shifting device unfastening the second connector from the port device by leaving from the lower end of the flange upon being set in the released position.

Preferably, the shifting device is slidable between the released and latched positions relative to the second tapered portion and perpendicularly to an axial direction of the second connector.

In still another preferred embodiment, the shifting device is rotatable between the released and latched positions about an axial direction of the second connector.

Preferably, the port device includes a female Luer tapered surface, formed in the opening between the first tapered portion and the fluid channel, and tapered at a taper angle different from a taper angle of the first tapered portion. Furthermore, a male Luer tapered surface is disposed with a related apparatus for the endoscope, for engagement with the female Luer tapered surface.

Accordingly, air-tightness or liquid-tightness can be ensured even in use of a plurality of connectors couplable selectively for connecting a related apparatus to the endoscope, because of functions of an engaging device, a fastening device and pusher.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
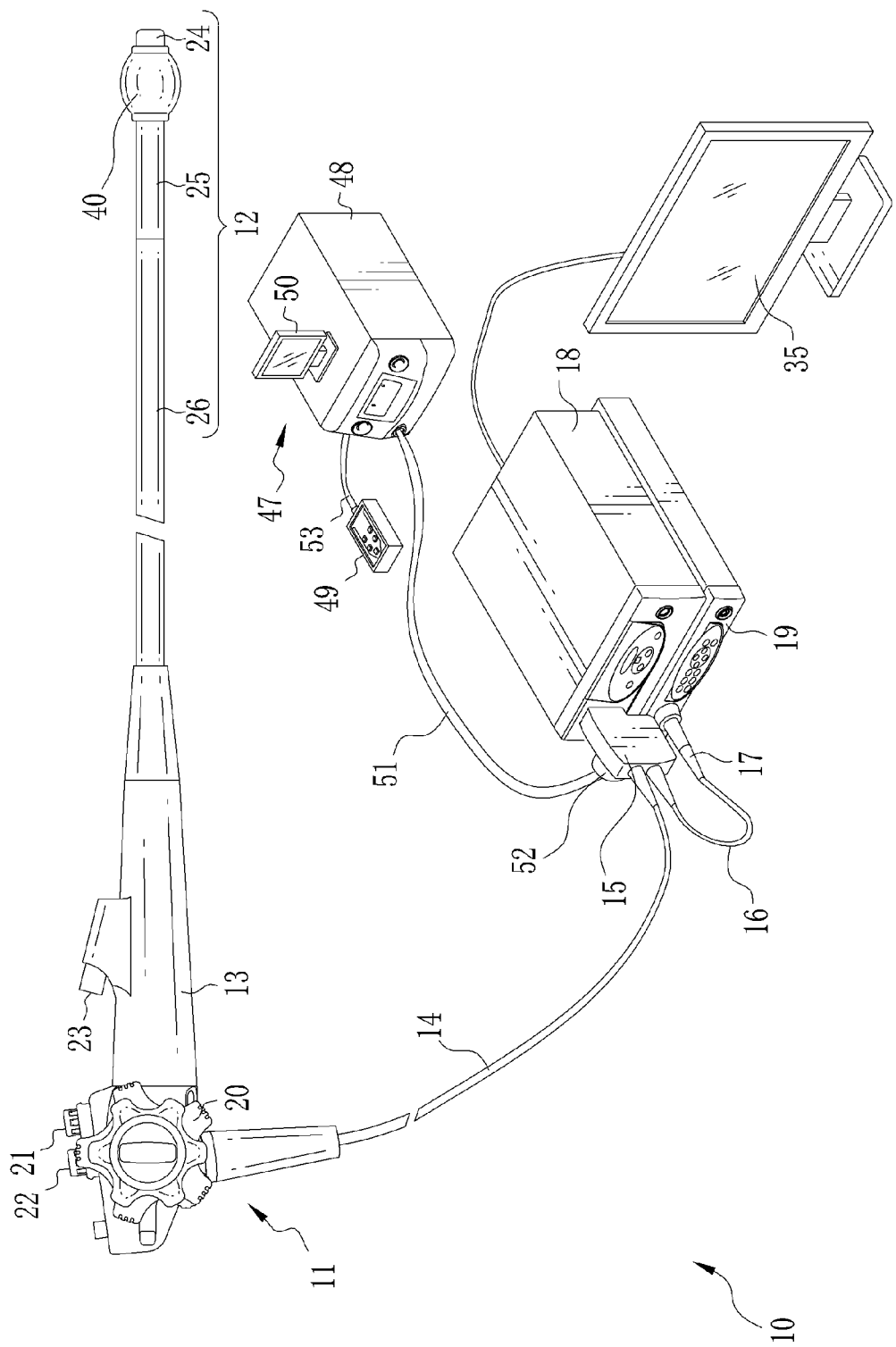
FIG. 1 is an explanatory view illustrating an endoscope system.

In FIG. 1, an endoscope system 10 has an electronic endoscope 11 with a balloon. The endoscope 11 has an elongated tube 12 or insertion tube and a grip handle 13. The elongated tube 12 is entered in a body cavity of a patient, for example, a large intestine of a gastrointestinal tract. The grip handle 13 is disposed at a proximal end of the elongated tube 12, and manipulated by a user or physician for imaging. A universal cable 14 extends from the grip handle 13. A light source connector 15 is disposed at a cable end of the universal cable 14. A branch cable 16 extends from the light source connector 15. A processor connector 17 is disposed at a cable end of the branch cable 16. The light source connector 15 is coupled to a light source apparatus 18 removably. The processor connector 17 is coupled to a processing apparatus 19 removably.

The grip handle 13 includes steering wheels 20, a fluid supply button 21 and a suction button 22. The fluid supply button 21 is operable for supplying air or water through an end of the elongated tube 12. A proximal instrument opening 23 is formed in the grip handle 13 on a proximal side for entry of a medical instrument for treatment, for example, electrocautery device.

The elongated tube 12 includes a tip device 24, a steering device 25 and a flexible device 26. The tip device 24 includes an image sensor for imaging an object in the body cavity. The steering device 25 at a proximal end of the tip device 24 is bendable for steering in various directions. The flexible device 26 at a proximal end of the steering device 25 extends flexibly. The flexible device 26 is as long as several meters for the tip device 24 to reach an object of interest. The steering device 25 is driven for steering in response to rotation of the steering wheels 20 of the grip handle 13. Thus, the tip device 24 can be directed in a desired direction.

Figure 2:
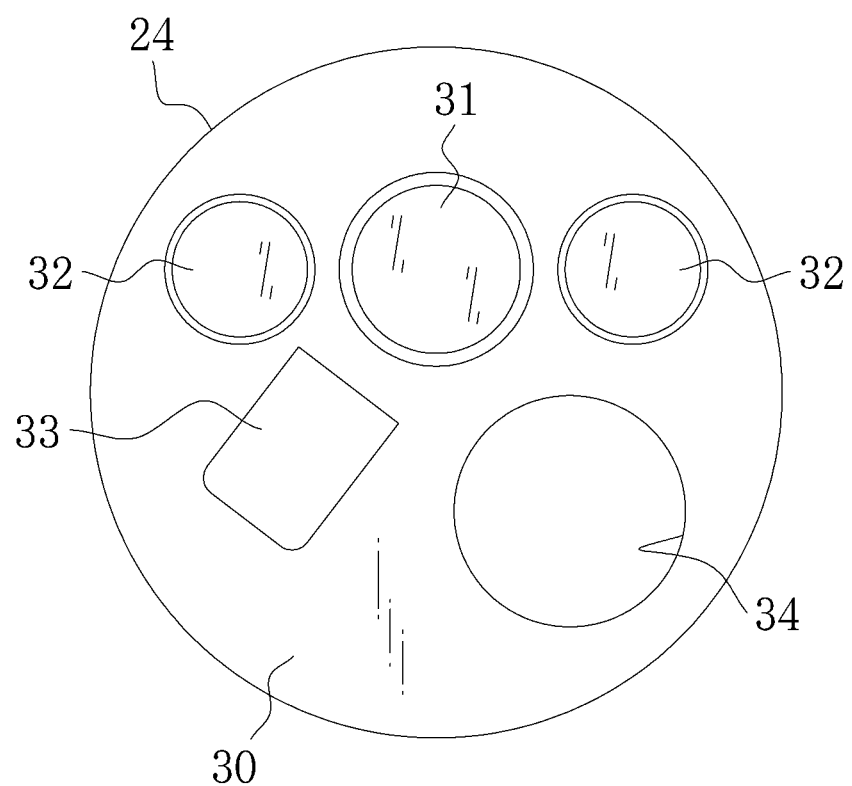
FIG. 2 is a front elevation illustrating a tip device of an endoscope.
Figure 3:
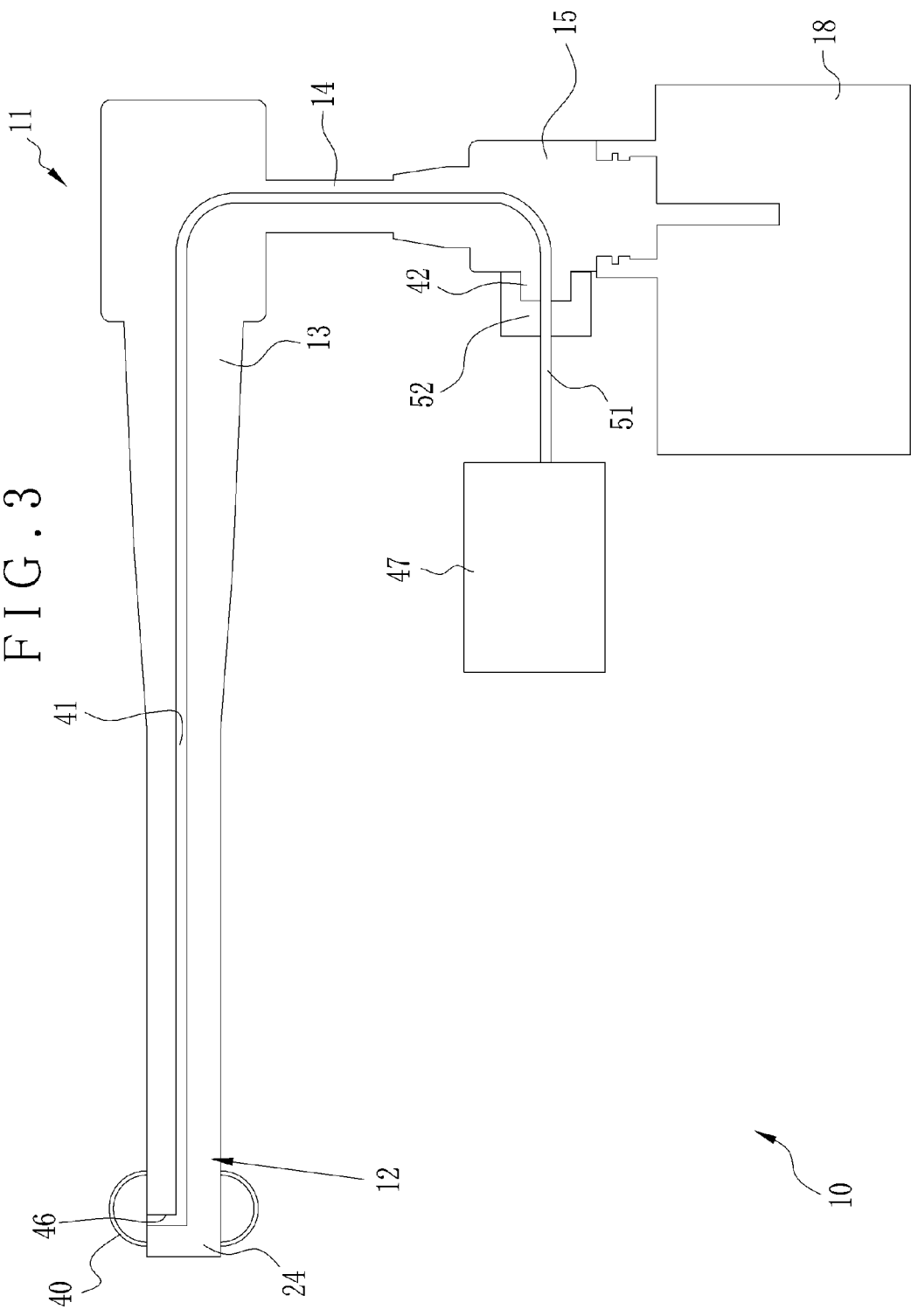
FIG. 3 is an explanatory view in a vertical section illustrating a fluid channel in the endoscope.

In FIG. 2, there are various elements on an end face 30 of the tip device 24, including a viewing window 31, lighting windows 32, a nozzle spout 33 for fluid, and a distal instrument opening 34. The viewing window 31 is disposed off-center in the end face 30. The lighting windows 32 are symmetric with each other with respect to the viewing window 31.

A lens system or optics and the image sensor are disposed on an inner side from the viewing window 31. The lens system receives image light from the object in the body cavity. The image sensor is a CCD or CMOS for imaging the object. A signal cable is disposed to extend through the elongated tube 12, the grip handle 13 and the tube of the universal cable 14 to the processor connector 17, and connects the image sensor to the processing apparatus 19. An image received through the viewing window 31 is focused on an imaging plane of the image sensor, and converted into an image signal. The processing apparatus 19 processes the image signal from the signal cable for image processing, and converts this into a video signal. A monitor display panel 35 of FIG. 1 is driven by the processing apparatus 19 to display an image of the video signal.

A distal end of a light guide device is disposed behind the lighting windows 32 for transmitting light from a light source in the light source apparatus 18. The light guide device is disposed to extend through the elongated tube 12, the grip handle 13 and the tube of the universal cable 14 to the light source connector 15. A proximal end of the light guide device is disposed in the light source connector 15. The light transmitted by the light guide device is applied to the object in the body cavity through the lighting windows 32.

The nozzle spout 33 in response to depression of the fluid supply button 21 blows air or water to the viewing window 31 from an air/water supply device incorporated in the light source apparatus 18. An instrument channel (not shown) is formed through the elongated tube 12. The distal instrument opening 34 is disposed at a distal end of the instrument channel. The proximal instrument opening 23 is disposed at a proximal end of the instrument channel. A distal end of a treatment device entered through the proximal instrument opening 23 is protruded from the distal instrument opening 34.

The endoscope 11 includes a balloon 40 and a fluid channel 41. The fluid channel 41 is disposed to extend through the elongated tube 12, the grip handle 13, the tube of the universal cable 14 and the light source connector 15. Fluid is passed through the fluid channel 41, and supplied to or drawn from the balloon 40. The fluid channel 41 is constituted by a flexible tube.

Figure 4:
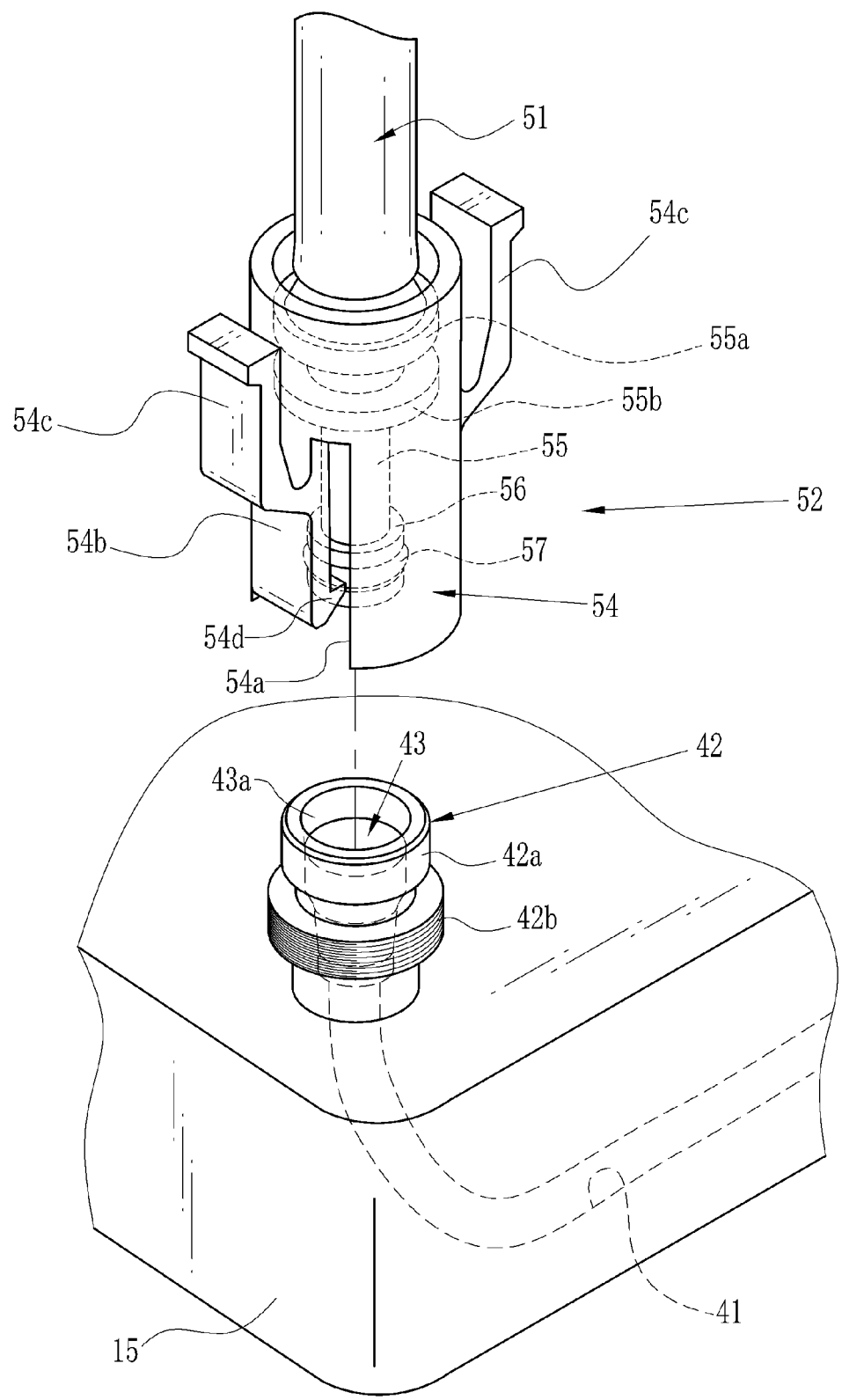
FIG. 4 is a perspective view illustrating a first connector and a port device.
Figure 5:
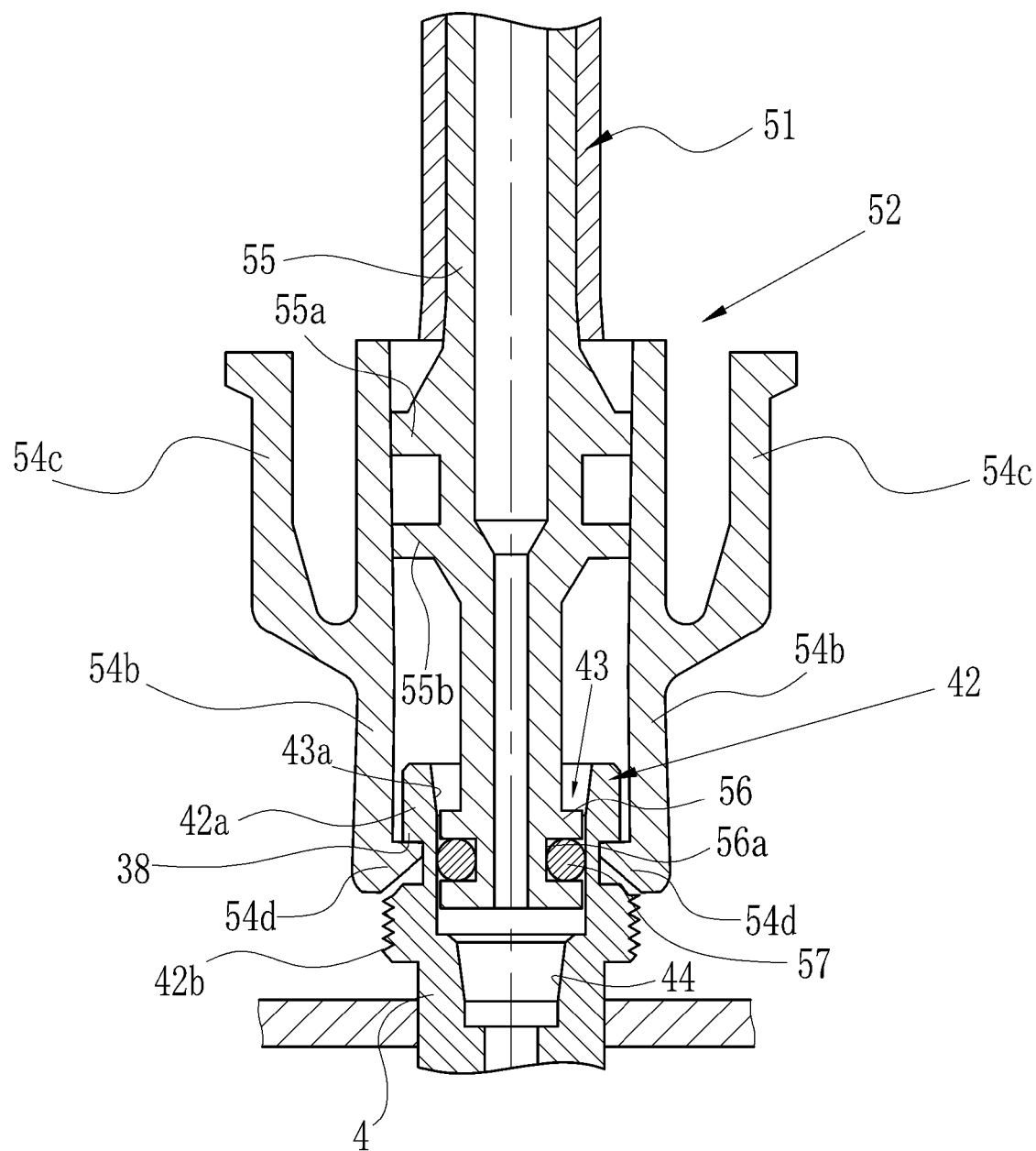
FIG. 5 is a cross section illustrating a fastened state of the first connector.

In FIGS. 4 and 5, a port device 42 or end sleeve is a portion of the light source connector 15 protruding from a flat surface at a proximal flow opening of the fluid channel 41. The port device 42 is the portion of metal as a projection on a housing of the light source connector 15. An opening 43 is defined inside the port device 42. An outer surface of the port device 42 extends to surround the opening 43. In the specification, a downward direction is defined as a direction toward the fluid channel 41 from the opening 43 of the port device 42. An upward direction is defined as a direction from the fluid channel 41 toward the opening 43. An end of elements of the port device 42 directed downwards is referred to as a lower end. An end of the elements of the port device 42 directed upwards is referred to as an upper end.

The port device 42 includes a flange 42a and a male thread 42b. The flange 42a continues from an upper surface and projects from a sleeve portion 4. The male thread 42b is disposed lower than the flange 42a. The male thread 42b is disposed at a predetermined interval from the flange 42a in an axial direction of the port device 42. A cleaning adapter 60 or second connector (fluid coupling) is fastened to the male thread 42b with threaded engagement to be described later.

A female tapered surface 43a or tapered bore surface (first tapered portion) is defined inside the opening 43 and positioned at an upper end of the port device 42. A male tapered surface 63a or tapered sealing surface (second tapered portion) is defined with the cleaning adapter 60 to be described later. The female tapered surface 43a tightly contacts the male tapered surface 63a. Also, a female Luer tapered surface 44 is defined in the opening 43 and positioned near to the fluid channel 41 lower than the female tapered surface 43a. The female Luer tapered surface 44 is adapted for engagement of a related apparatus in a shape of a male Luer tapered surface, for example, a syringe (68) for injecting a liquid drug. The female Luer tapered surface 44 is tapered at a taper angle different from that of the female tapered surface 43a.

The balloon 40 is disposed on the tip device 24 of the elongated tube 12 removably. The balloon 40 is formed from rubber with resiliency in a bag shape. The balloon 40 includes first and second ends with a small diameter and a bag portion at the center. To mount the balloon 40 on the tip device 24, at first the tip device 24 is passed through the balloon 40, which is set on the tip device 24 in a suitable position. Then rings of rubber are fitted on the first and second ends to attach the balloon 40 on the tip device 24.

The fluid channel 41 is constituted by a flexible tube, and has a distal end which is not open at the distal end surface of the tip device 24 with the balloon 40. A flow opening 46 is formed in a peripheral surface of the tip device 24 and distally from the fluid channel 41. The flow opening 46 is positioned at the balloon 40, and supplies and draws fluid to inflate and deflate the balloon 40. The proximal end of the fluid channel 41 communicates with the opening 43. There is a balloon control apparatus 47 to which the fluid channel 41 is connected.

The balloon control apparatus 47 supplies fluid (air) to or draws fluid from the balloon 40 of the endoscope 11. The balloon control apparatus 47 includes an apparatus housing 48, a manual switching device 49 for control, and a special monitor display panel 50 for the balloon. The apparatus housing 48 has a pump, sequencer and the like.

The balloon control apparatus 47 supplies the balloon 40 with fluid for inflation, and also keeps the balloon 40 inflated by controlling the fluid at a predetermined high pressure. Also, the balloon control apparatus 47 draws fluid from the balloon 40 for deflation, and also keeps the balloon 40 deflated by controlling the fluid at a lower pressure. The special monitor display panel 50 displays information of the balloon 40 in the course of the inflation and deflation, such as a pressure value, inflating and deflating statuses and the like of the balloon 40. It is also possible for the monitor display panel 35 to display the information of the balloon 40 in a superimposed form on an endoscopic image of the endoscope 11.

Various elements are disposed on a front panel of the apparatus housing 48 of the balloon control apparatus 47, including a power switch, stop switch, pressure indicator (not shown) for the balloon 40. The stop switch is operable for emergency. The pressure indicator is a panel for indicating the pressure value of the balloon 40, and displays an error code upon occurrence of abnormality of the balloon 40, for example, breakage.

A flow tube 51 is connected to the front panel of the apparatus housing 48 for supplying and drawing fluid with the balloon 40. A check valve device (not shown) or anti-backflow device is provided in a connecting portion between the flow tube 51 and the balloon control apparatus 47, and is mounted on the front panel of the apparatus housing 48 removably. The check valve device includes a housing of a disk shape and a separation filter. The housing is mounted on the front panel. The separation filter is contained in the housing. Assuming that the balloon 40 is broken, the check valve device prevents body liquid or the like from flowing into the balloon control apparatus 47.

A first connector 52 (fluid coupling) is disposed at a distal end of the flow tube 51. Coupling of the first connector 52 to the light source connector 15 of the endoscope 11 can connect the flow tube 51 to the fluid channel 41 of the endoscope 11. The first connector 52 is initially packaged in a sterilized state, removed from the packaging for use, and coupled to the flow tube 51 and the light source connector 15. The first connector 52 is a disposable type, and is discarded after use of one time or a small number of times before updating to a new connector. Note that the small number of times is 10 times or less.

Various switches are incorporated in the manual switching device 49, such as a stop switch similar to that in the apparatus housing 48, and a changeover switch for applying positive or negative pressure to the balloon 40 by turning on and off an overtube device. A cable 53 electrically connects the manual switching device 49 to elements in the apparatus housing 48.

Figure 6:
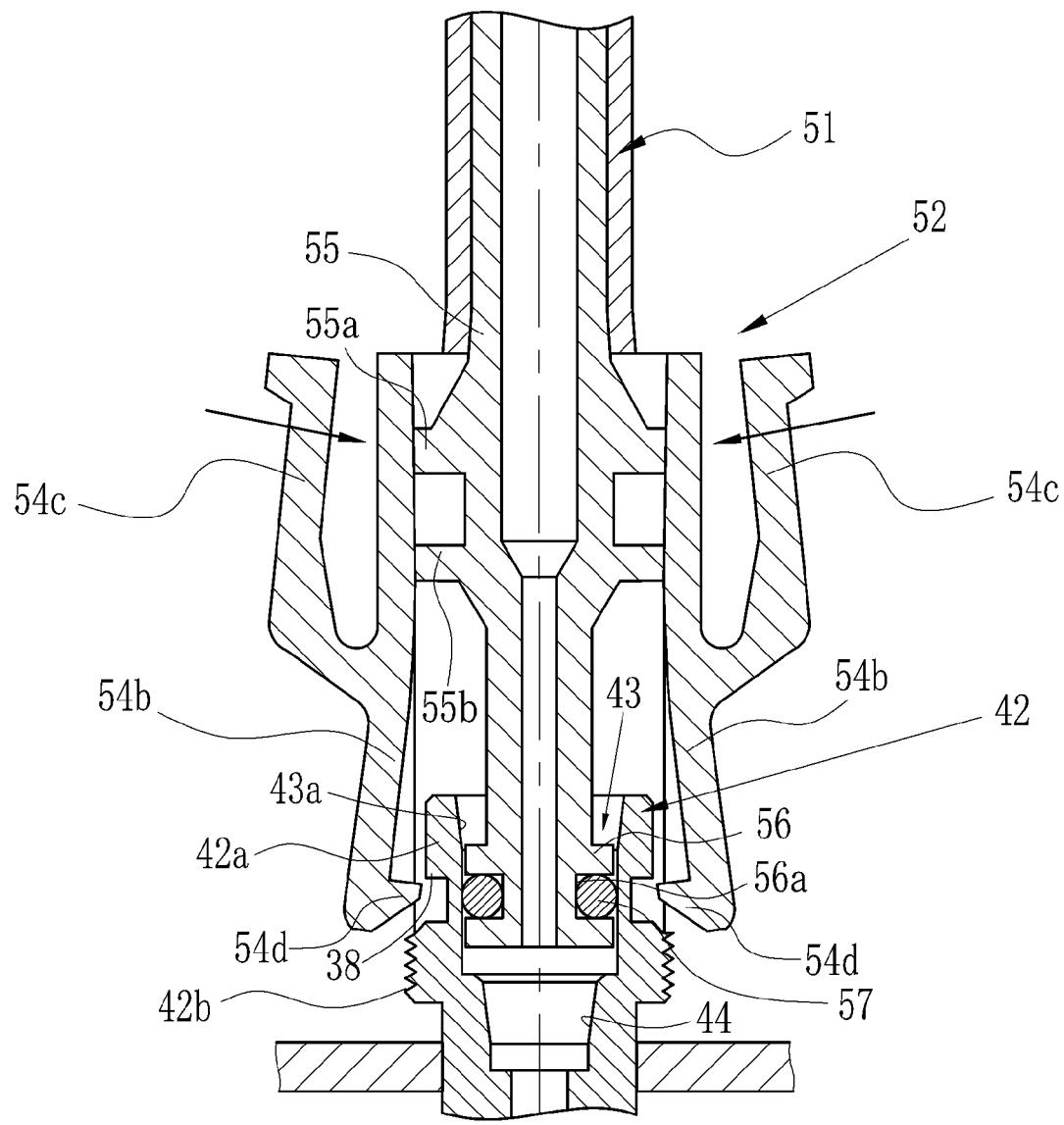
FIG. 6 is a cross section illustrating removal of the first connector.

In FIGS. 5 and 6, the first connector 52 includes a connector housing 54 and a flow sleeve 55. The connector housing 54 is formed from plastic material or resin, and has upper and lower open ends. The lower end of the connector housing 54 is directed to the light source connector 15.

The flow sleeve 55 is disposed in the connector housing 54 in alignment in the axial direction. Annular ridges 55a and 55b are formed with the flow sleeve 55 and have larger diameters intermediately in the axial direction. The annular ridges 55a and 55b are tightly fitted on an inner surface of the connector housing 54 to attach the connector housing 54 to the flow sleeve 55. The flow sleeve 55 is positioned in the opening 43 by setting the port device 42 in the connector housing 54. The flow tube 51 extends from an upper side of the annular ridge 55a at an upper end of the flow sleeve 55.

The flow sleeve 55 is formed from resin. An annular support projection 56 is disposed at a lower end of the flow sleeve 55, and entered in the opening 43. An O-ring 57 of rubber as a sealing structure or seal packing is disposed around the support projection 56. A groove 56a is formed in the support projection 56, and receives the O-ring 57 for attachment. An outer diameter of the O-ring 57 upon engagement with the flow sleeve 55 is slightly larger than an inner diameter of the opening 43. The O-ring 57 is deformed to contact the opening 43 tightly upon entry of the flow sleeve 55 in the opening 43. It is possible to seal the support projection 56 in the opening 43 air-tightly and liquid-tightly by pressure of the O-ring 57 to those.

The connector housing 54 includes two cutouts 54a, two arms 54b, two finger grip portions 54c and two engaging claws 54d (engaging device). The cutouts 54a are extended in the axial direction from a lower end to a lower side of the annular ridge 55b. The arms 54b are disposed inside the cutouts 54a. The finger grip portions 54c project from upper ends of the arms 54b outwards. The engaging claws 54d project inwards from lower ends of the arms 54b. Those are arranged in a rotationally symmetric manner with an angle of 180 degrees. The arms 54b are resilient in a form of plates extending in the axial direction of the connector housing 54 from the annular ridge 55b.

The finger grip portions 54c are shaped as plates extending upwards from the arms 54b with an inclination, and have resiliency. In case the finger grip portions 54c are depressed toward the center of the connector housing 54, the arms 54b move together with the finger grip portions 54c. Lower ends of the arms 54b protrude out of the cutouts 54a. In case the finger grip portions 54c are free without push, the arms 54b are set in the original position by resiliency.

Engagement of the port device 42 of the light source connector 15 with the inner surface of the connector housing 54 causes the engaging claws 54d to move over the flange 42a. The first connector 52 is coupled to the port device 42 by engagement of the engaging claws 54d with a lower end 38 (rear end) of the flange 42a. See FIG. 5. In case the finger grip portions 54c are depressed, the arms 54b are moved as described above, to shift the engaging claws 54d radially outwards with the connector housing 54. See FIG. 6. Thus, the first connector 52 becomes removable from the port device 42 upon disengaging the engaging claws 54d from the flange 42a. Note that the engaging claws 54d are formed in a smaller size than a groove width between the flange 42a and the male thread 42b for preventing interference of the male thread 42b with the engagement between the engaging claws 54d and the flange 42a.

The flow tube 51 is connected with the fluid channel 41 by coupling the port device 42 to the first connector 52, so that the balloon control apparatus 47 is ready to supply fluid to or draw fluid from the balloon 40.

Figure 7:
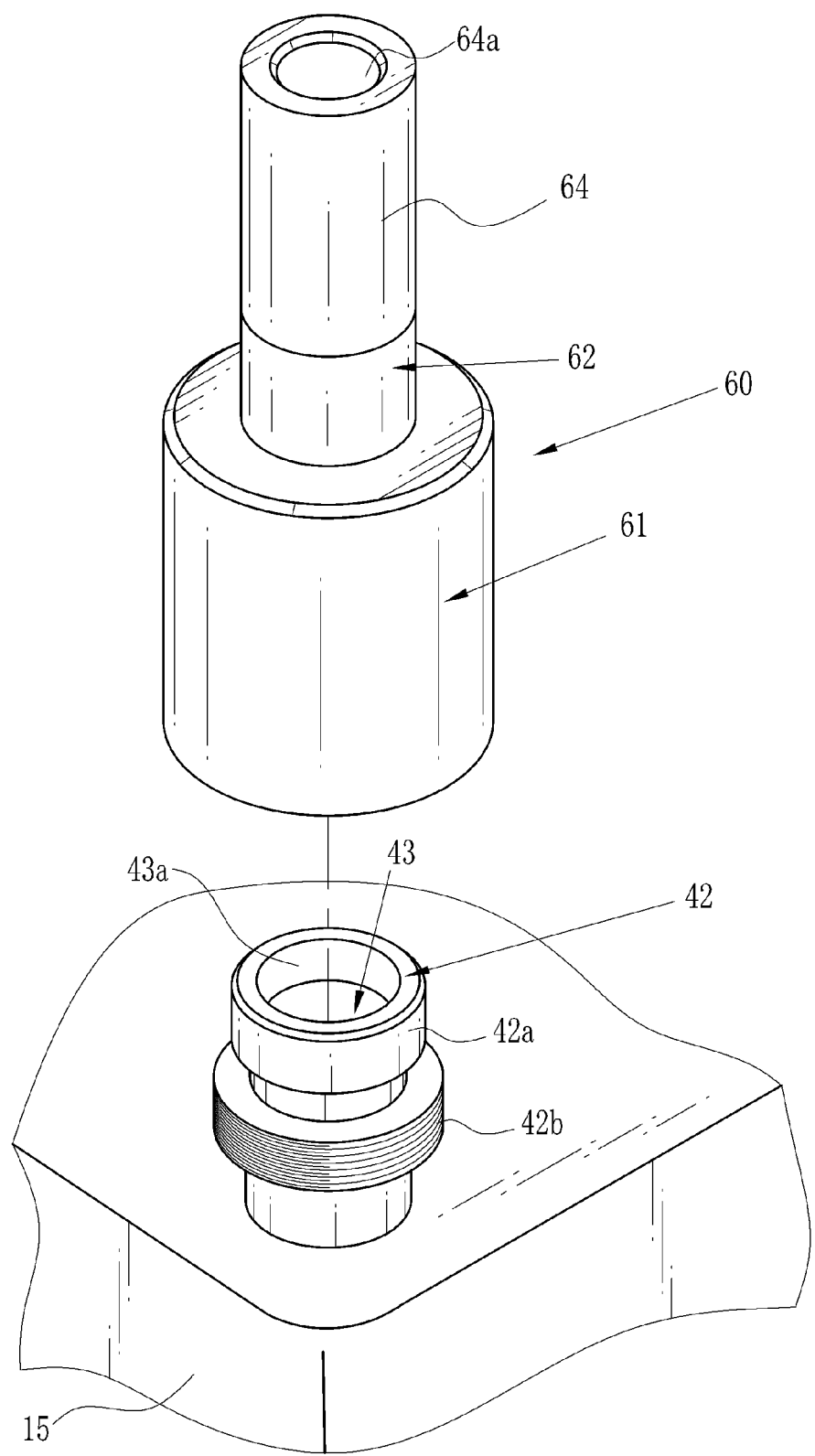
FIG. 7 is a perspective view illustrating a cleaning adapter (second connector) and the port device.
Figure 8:
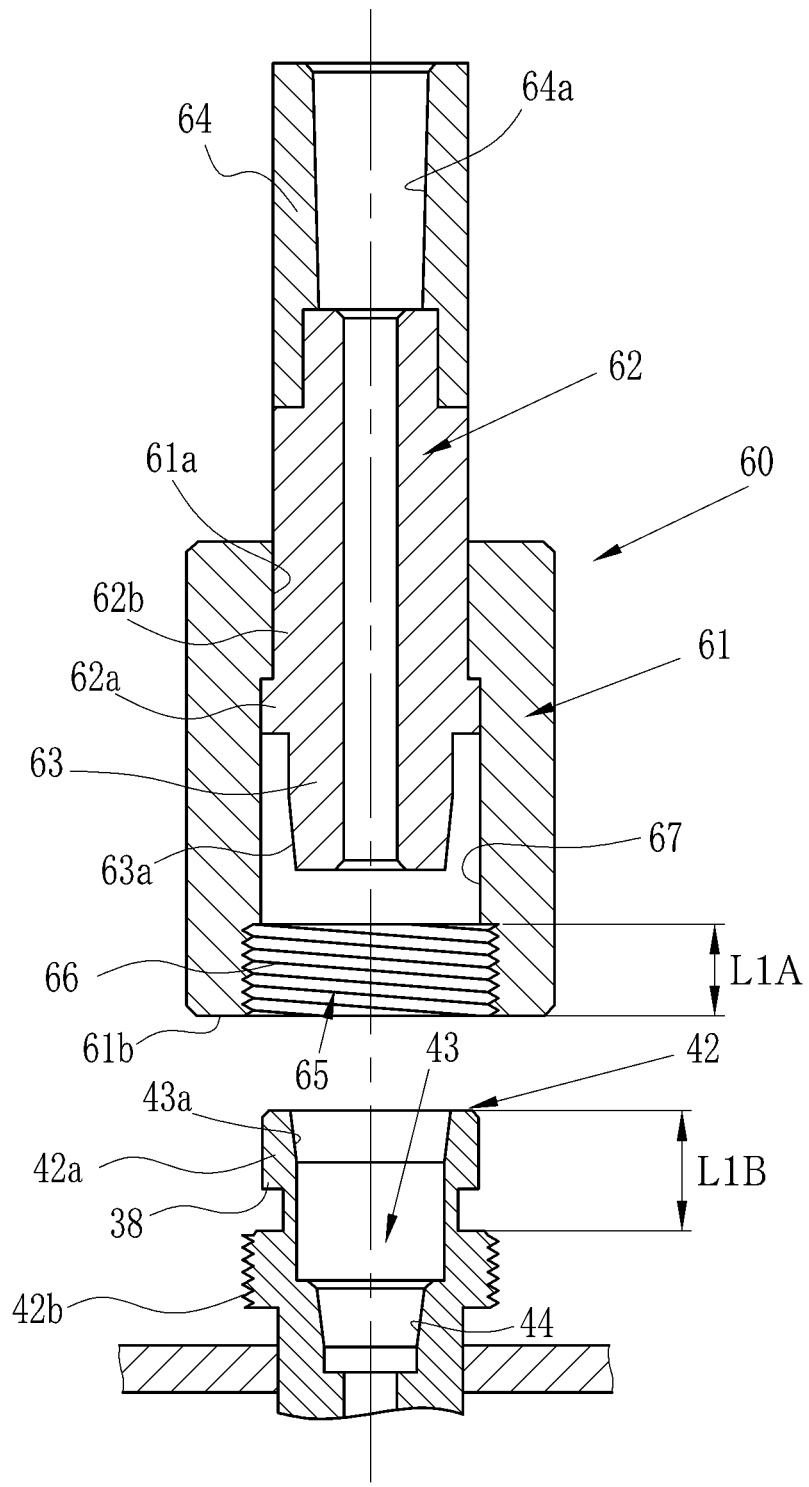
FIG. 8 is a cross section illustrating the same as FIG. 7.
Figure 9:
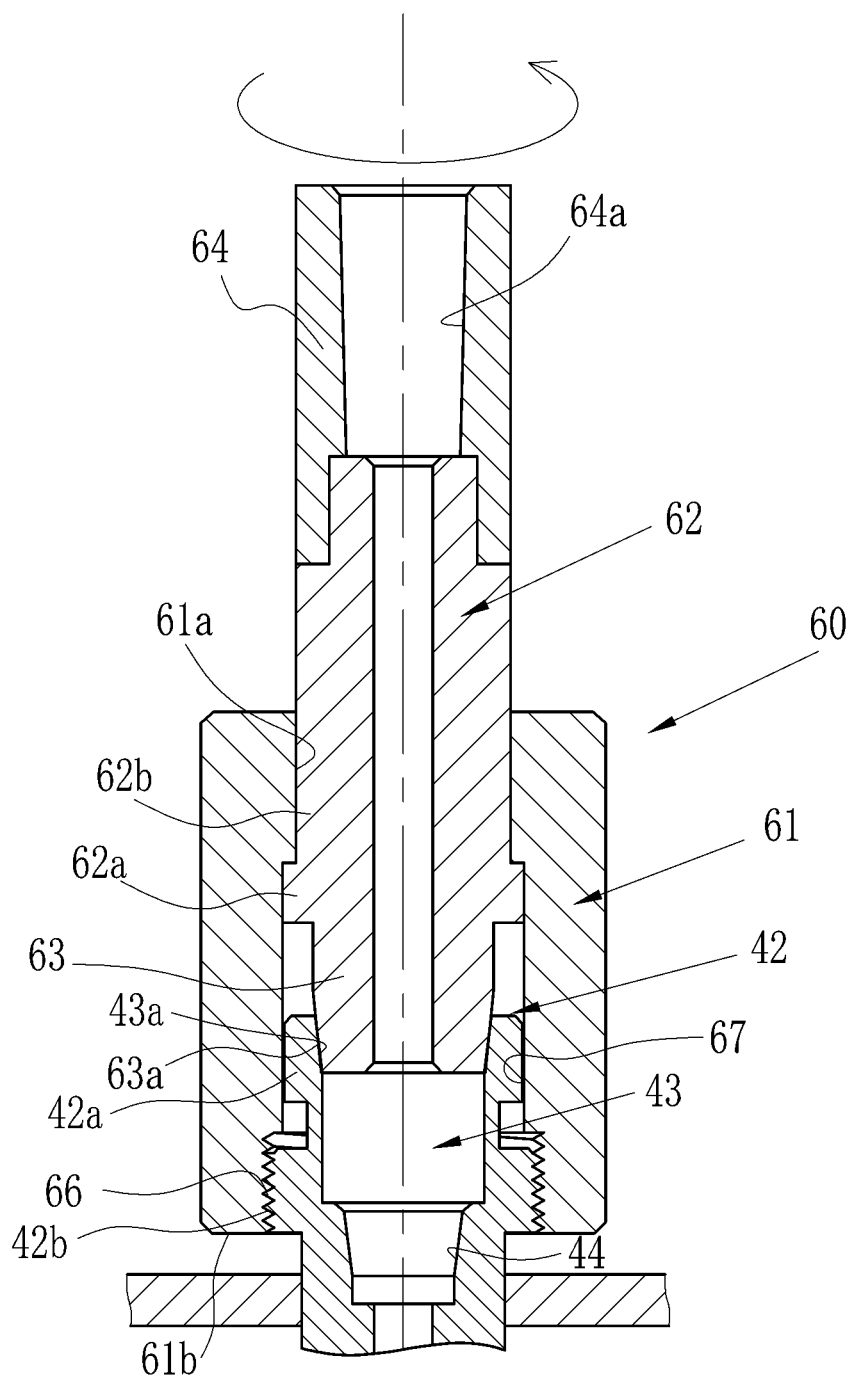
FIG. 9 is a cross section illustrating a fastened state of the cleaning adapter.

To clean the endoscope 11, the first connector 52 is removed from the endoscope 11 as illustrated in FIGS. 7-9. The cleaning adapter 60 is mounted on the endoscope 11. The first connector 52 and the cleaning adapter 60 are selectively couplable to the port device 42. Shapes and coupling methods of the first connector 52 and the cleaning adapter 60 are different from one another, so that no error occurs in the connection.

All of elements in the cleaning adapter 60 are metallic, inclusive of a connector housing 61 and a coupling sleeve 62. The cleaning adapter 60 is usable repeatedly as a reusable type. The connector housing 61 is a barrel, and has a hole opening 65 at a lower end directed to the light source connector 15. An inner surface 61a of the connector housing 61 has a smaller inner diameter than that of a female thread 66 (fastening device) and a guide surface 67 to be described later.

The coupling sleeve 62 is axially fitted in the connector housing 61. A male tapered portion 63 is formed on the coupling sleeve 62 and projects downwards to the port device 42. The male tapered surface 63a is included in the male tapered portion 63 with a taper angle in compliance with the female tapered surface 43a of the opening 43, and seals the cleaning adapter 60 and the port device 42 air-tightly or water-tightly by contacting the female tapered surface 43a. The coupling sleeve 62 includes a large diameter portion 62a and a small diameter portion 62b. The large diameter portion 62a is higher than the male tapered surface 63a with a larger diameter. The small diameter portion 62b is higher than the large diameter portion 62a with a smaller diameter. The small diameter portion 62b is fitted on the inner surface 61a of the connector housing 61 to attach the coupling sleeve 62 to the connector housing 61.

An adapter sleeve 64 is disposed at an upper end of the coupling sleeve 62. A syringe 68 for cleaning is coupled to the adapter sleeve 64. The adapter sleeve 64 has a cylindrical outer surface, and a female tapered surface 64a or tapered bore surface, which is disposed at the upper end and inclined at a taper angle according to the syringe 68 to be described later.

The connector housing 61 has a distal end surface 61b. The male tapered surface 63a is disposed higher than the distal end surface 61b on an inner side. The hole opening 65 in the connector housing 61 is directed to the port device 42. The female thread 66 is formed with the hole opening 65. The guide surface 67 is disposed around the male tapered surface 63a and higher than the female thread 66. The guide surface 67 has an inner diameter which is larger than that of the female thread 66 and larger than an outer diameter of the flange 42a.

The female thread 66 is helically engaged with the male thread 42b of the port device 42. A size L1A of the female thread 66 in the axial direction is smaller than a distance L1B from the upper end of the port device 42 to the male thread 42b in the axial direction. Thus, the female thread 66 is prevented from engagement with the male thread 42b while the flange 42a moves to pass the female thread 66. Upon passing the female thread 66, the flange 42a moves to the guide surface 67. The guide surface 67 guides the port device 42 by contacting the outer surface of the flange 42a. Thus, the male tapered surface 63a is axially aligned with the female tapered surface 43a. Further entry of the flange 42a to the inner side of the connector housing 61 helically engages the male thread 42b with the female thread 66. The male tapered surface 63a comes to contact the female tapered surface 43a.

It is important to keep sufficient stroke for aligning the male tapered surface 63a with the female tapered surface 43a axially with high precision, and to construct the port device 42 compactly without excessive enlargement. To this end, it is preferable to set a difference value (L1B−L1A) equal to or more than 1 mm and equal to or less than 3 mm, where L1B is the distance from the upper end of the port device 42 to the male thread 42b in the axial direction, and L1A is the size of the female thread 66 in the axial direction.

The female thread 66 is helically engaged with the male thread 42b to fasten the cleaning adapter 60 on the port device 42, and also presses the male tapered surface 63a to the female tapered surface 43a. Rotation of the connector housing 61 in a direction to engage the female thread 66 with the male thread 42b helically moves the connector housing 61 toward the port device 42 according to the threaded engagement of the male and female threads 42b and 66. Thus, the male tapered surface 63a is pressed to the female tapered surface 43a.

To use the endoscope 11, the first connector 52 of the balloon control apparatus 47 is coupled to the light source connector 15. The light source connector 15 is coupled to the light source apparatus 18. The processor connector 17 is coupled to the processing apparatus 19. A user or physician enters the elongated tube 12 of the endoscope 11 in a body cavity, and inflates or deflates the balloon 40 by manipulating the manual switching device 49 of the balloon control apparatus 47 as required.

Figure 10:
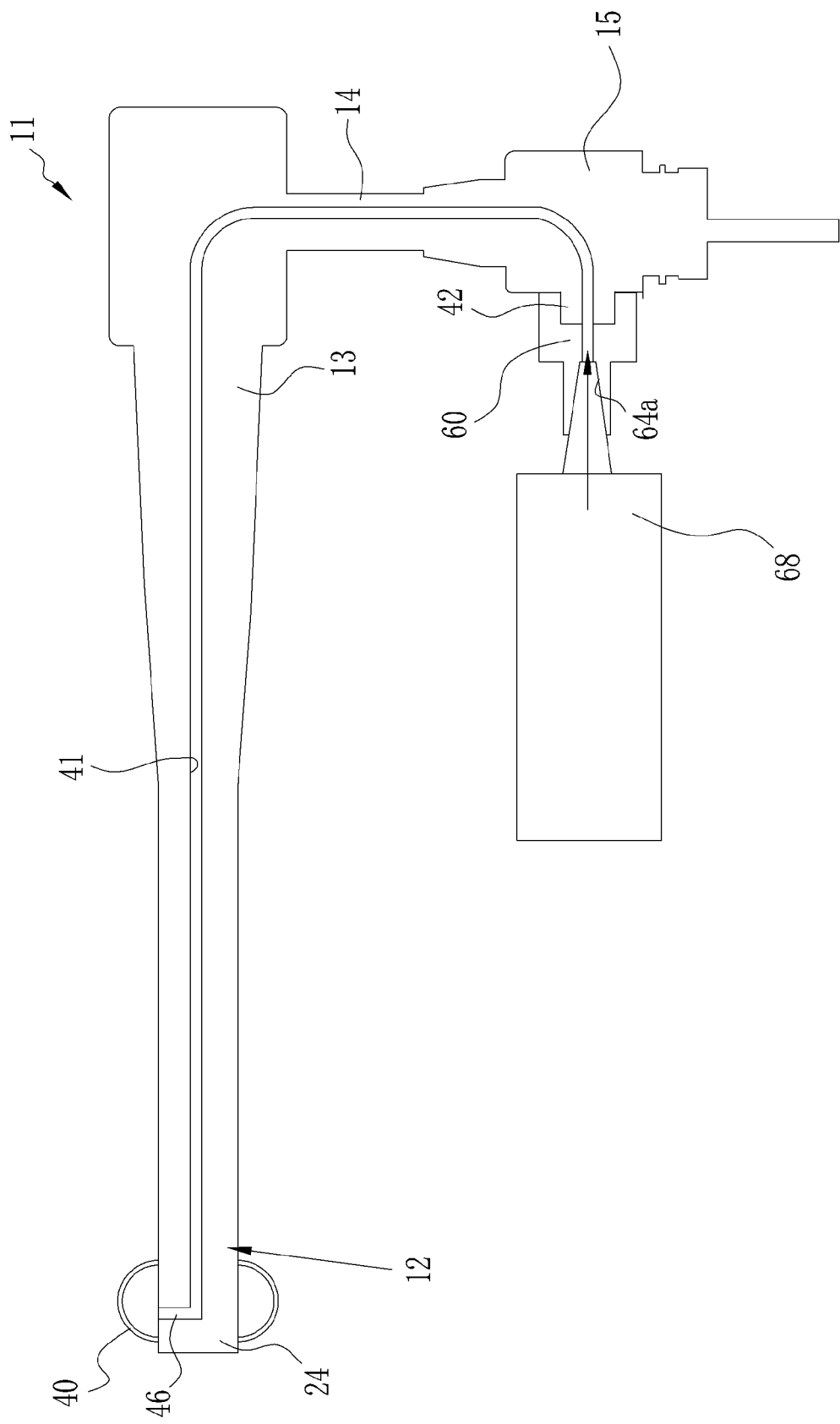
FIG. 10 is an explanatory view in a vertical section illustrating arrangement for cleaning the endoscope.

The operation of cleaning the endoscope 11 constructed above is described next. In FIG. 10, the balloon 40 and the first connector 52 of the balloon control apparatus 47 are removed from the endoscope 11 for the purpose of cleaning. The cleaning adapter 60 is coupled to the port device 42 of the light source connector 15. The syringe 68 with a tapered shape of the tip is set on the female tapered surface 64a of the cleaning adapter 60, so as to supply cleaning liquid. Note that a method of supplying cleaning liquid is not limited to the embodiment. For example, a flow channel of a tube cleaning apparatus can be coupled with the coupling sleeve 62 for continuing supply of cleaning liquid from the tube cleaning apparatus. The cleaning liquid from the syringe 68 is passed through the cleaning adapter 60 to the fluid channel 41. Then the fluid channel 41 can be cleaned.

As described heretofore, the flow sleeve 55 and the connector housing 54 of the first connector 52 is formed from resin in the endoscope system 10. The O-ring 57 is squeezed between the flow sleeve 55 and the port device 42. Thus, air-tightness and liquid-tightness with the port device 42 can be maintained even at a low cost, with an advantage in the use for a disposable type of connector. Also, the male thread 42b is disposed lower than the flange 42a at a predetermined interval. Breakage of the engaging claws 54d (engaging device) upon contacting the male thread 42b can be prevented.

As all of the elements in the cleaning adapter 60 including the coupling sleeve 62 are metallic, the cleaning adapter 60 is durable enough for repeated use. As the male tapered surface 63a is axially aligned with the female tapered surface 43a by the guide surface 67, the male tapered surface 63a can reliably contact the female tapered surface 43a. Also, the male thread 42b is helically engaged with the female thread 66 (fastening device) to press the male tapered surface 63a to the female tapered surface 43a, the coupling with the port device 42 can be tightened to ensure airtightness and liquid-tightness.

It is possible to prevent an error in the connection because of a difference in the shape between the first connector 52 and the cleaning adapter 60. The female Luer tapered surface 44 of the port device 42 is engageable with a related apparatus of a special male Luer tapered surface, and is effective in preventing an error in the connection.

Figure 11:
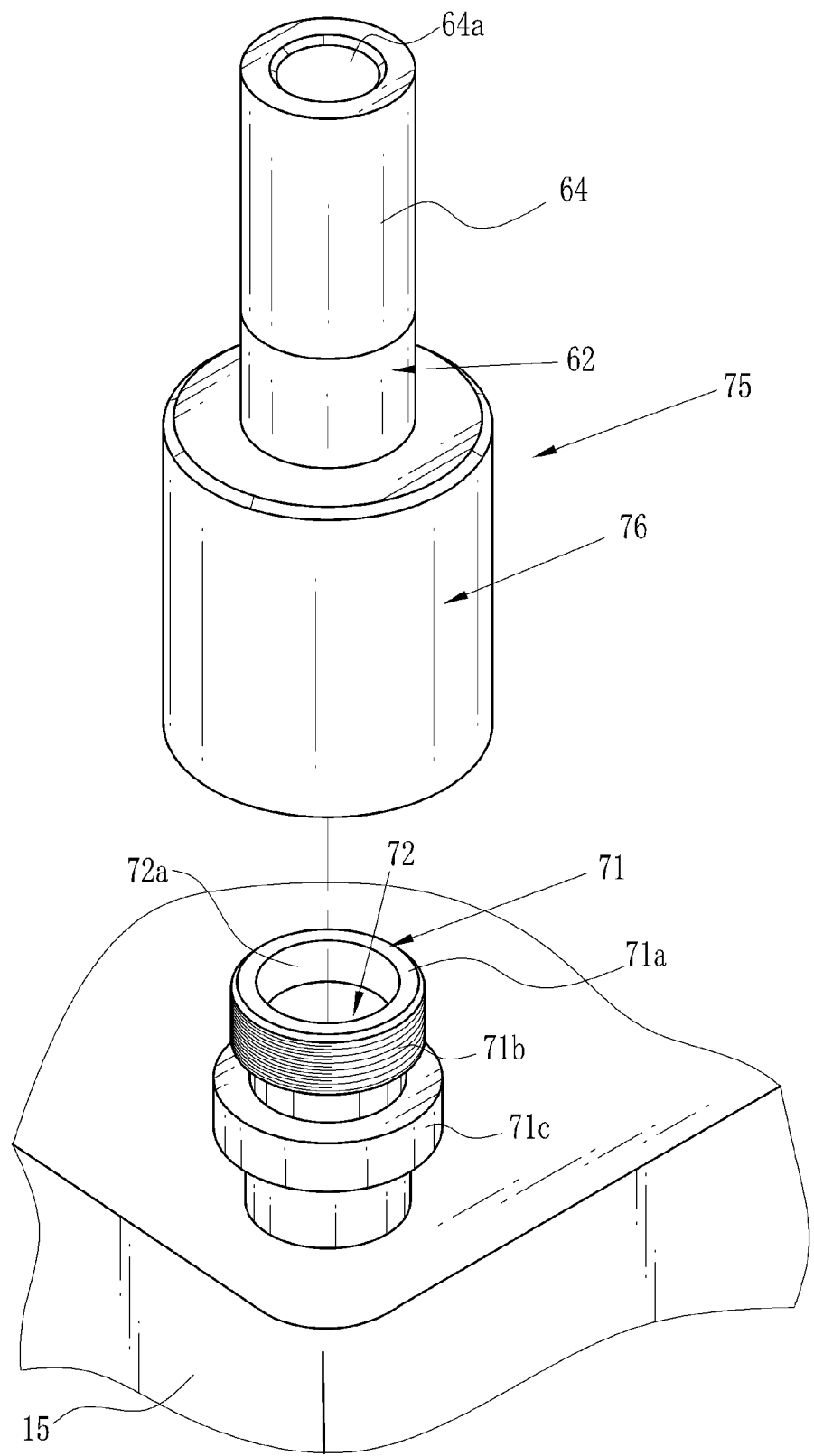
FIG. 11 is a perspective view illustrating a second preferred combination of a cleaning adapter and a port device.
Figure 12:
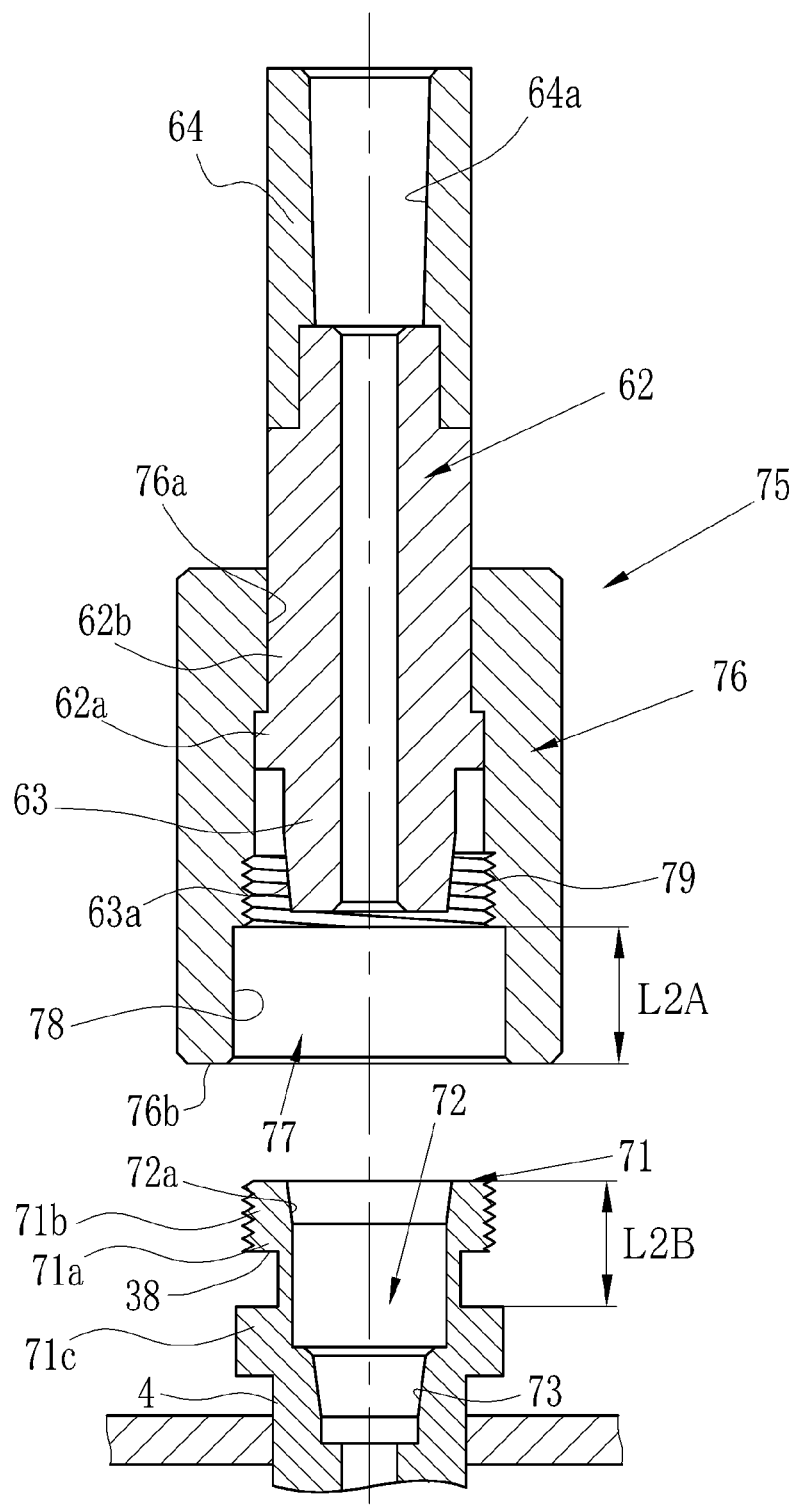
FIG. 12 is a cross section illustrating the same as FIG. 11.
Figure 13:
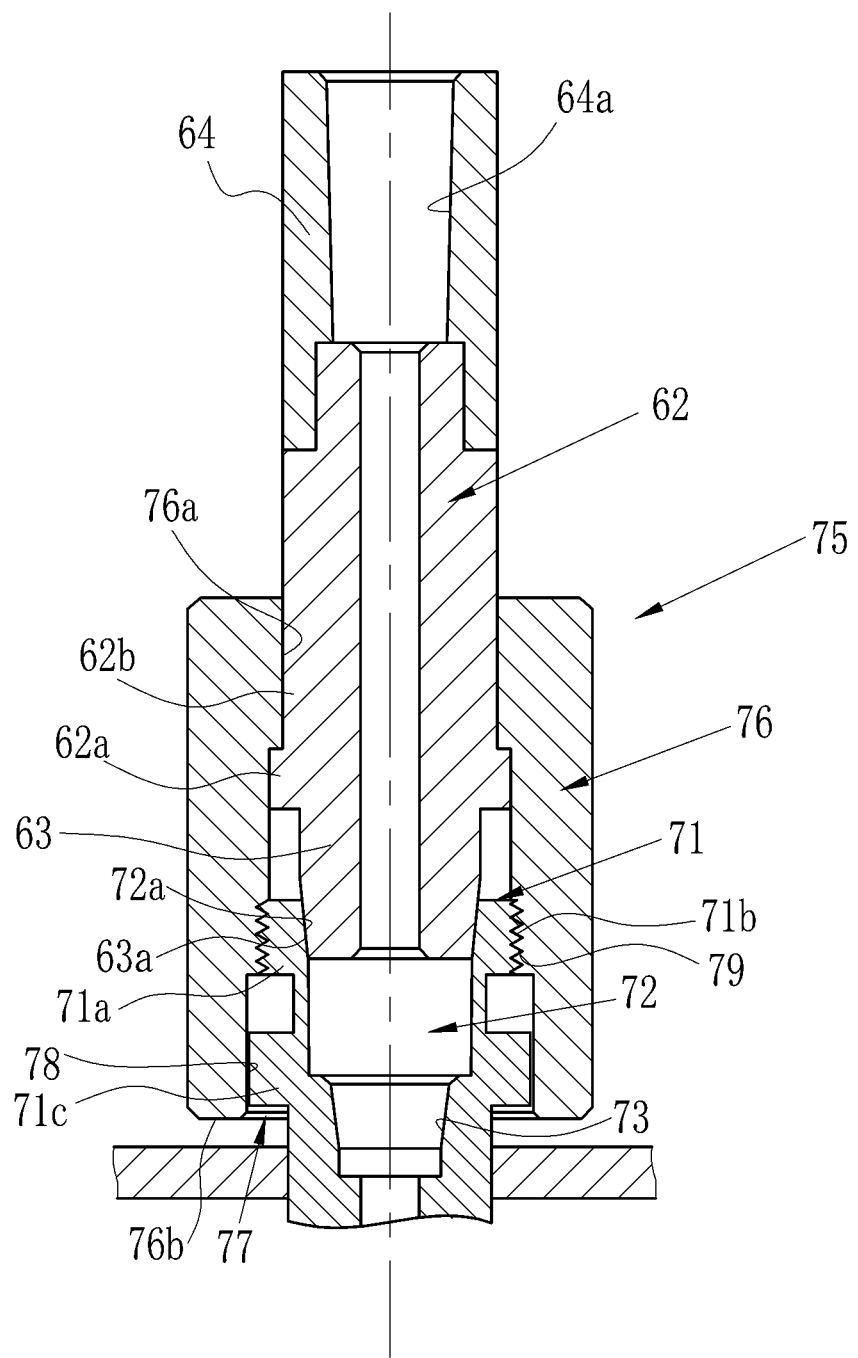
FIG. 13 is a cross section illustrating a fastened state of the cleaning adapter.
Figure 14:
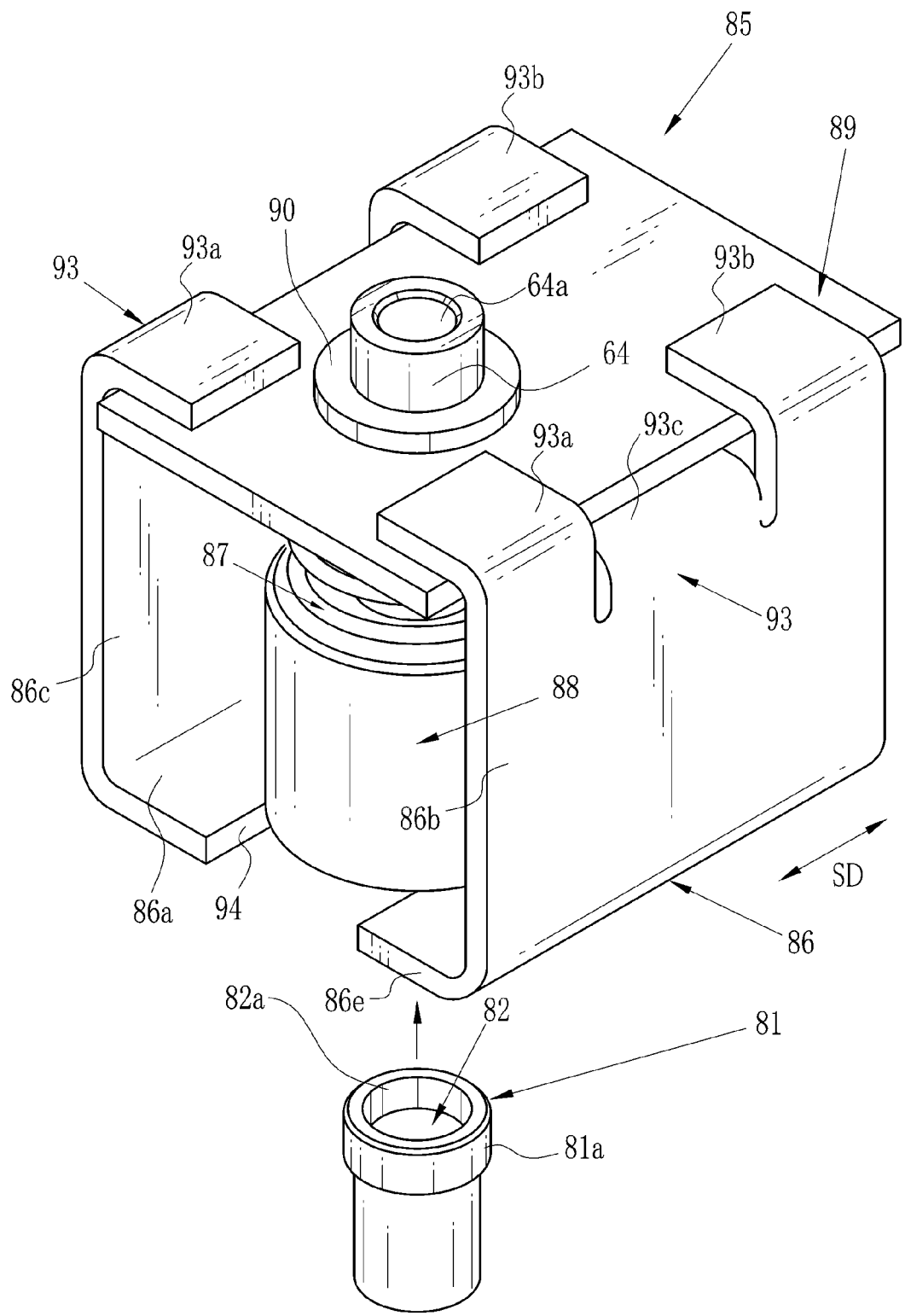
FIG. 14 is a perspective view illustrating a third preferred combination of a cleaning adapter and a port device.
Figure 15:
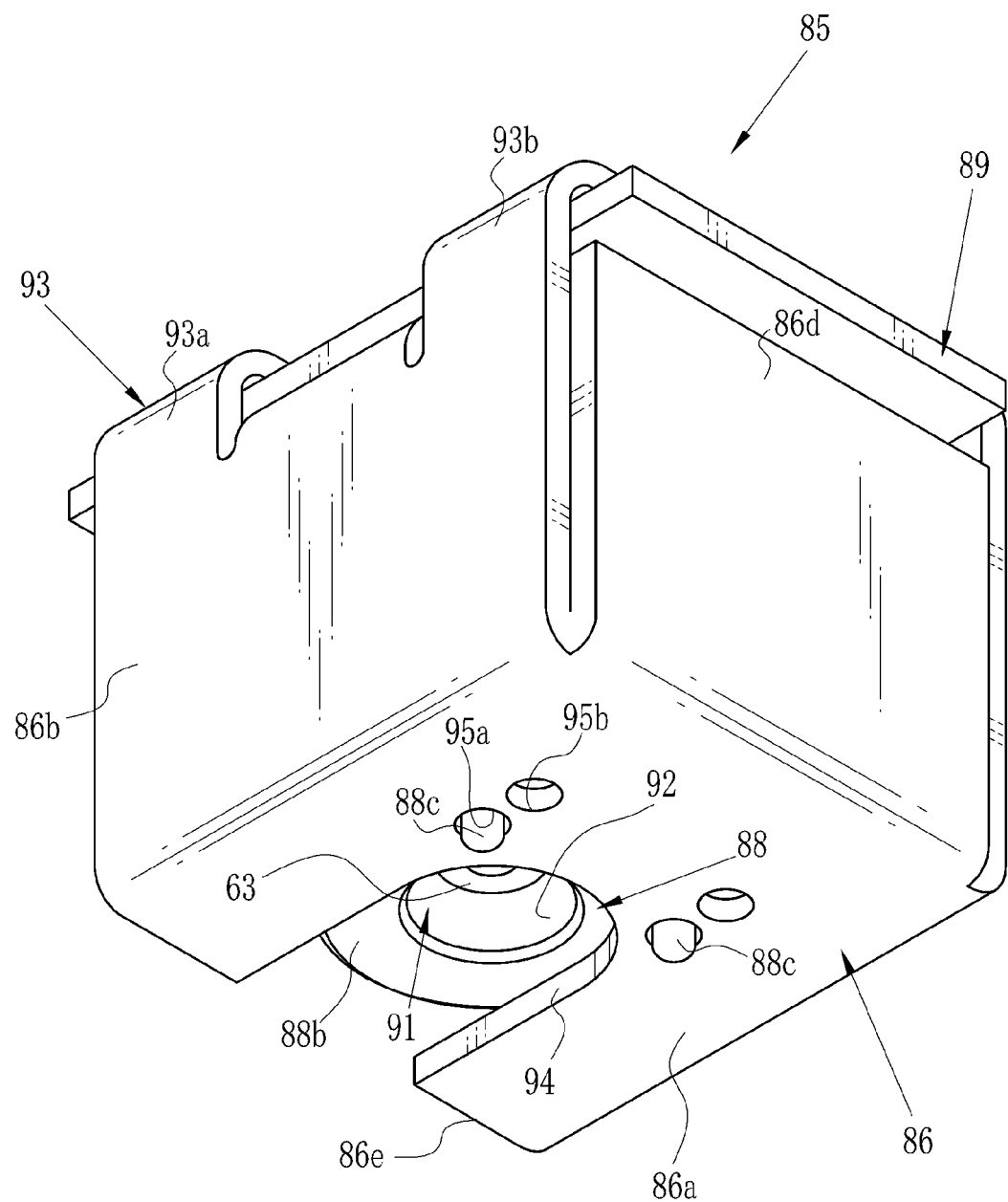
FIG. 15 is a bottom perspective view illustrating the cleaning adapter.
Figure 16:
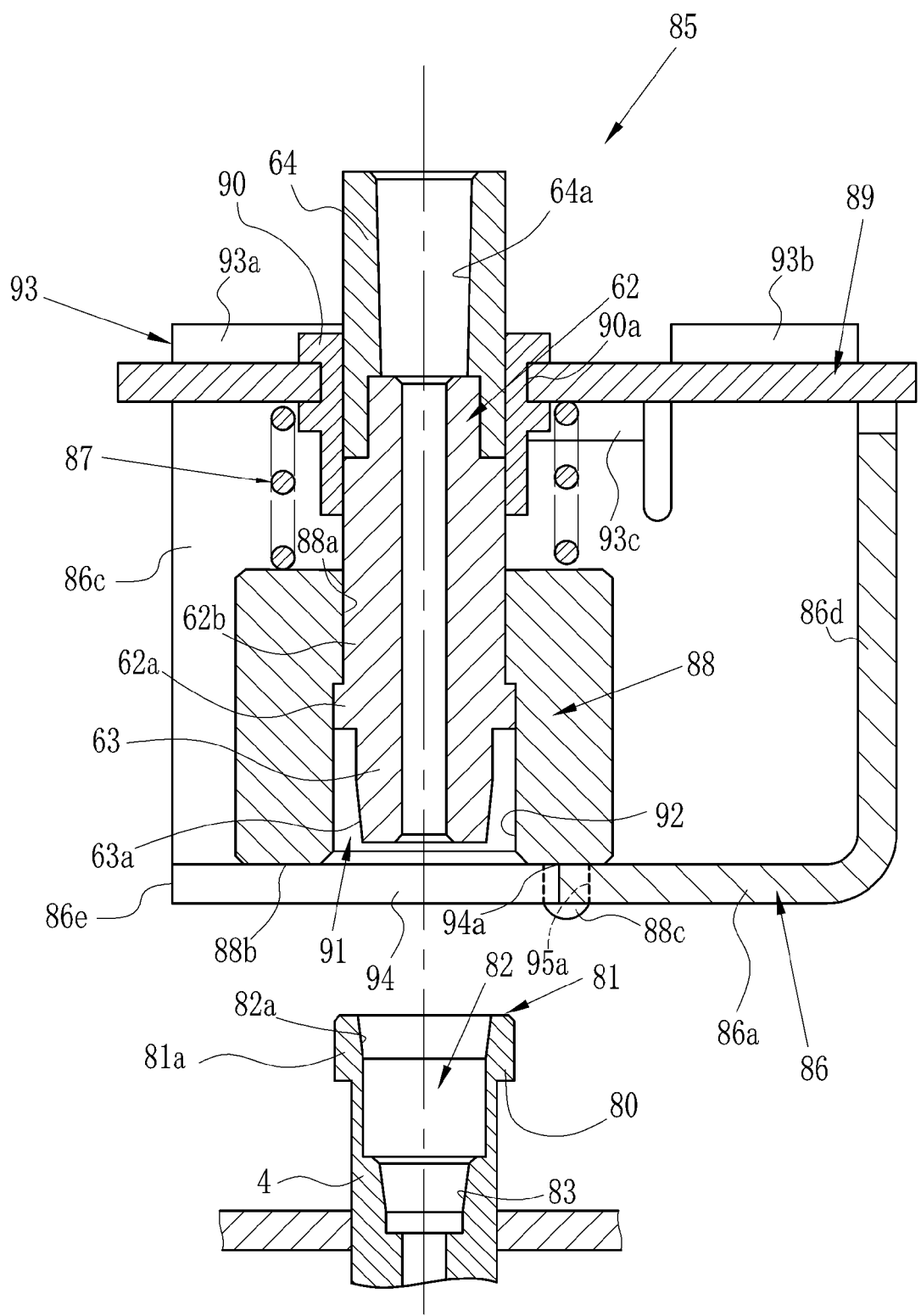
FIG. 16 is a cross section illustrating the cleaning adapter and the port device.
Figure 17:
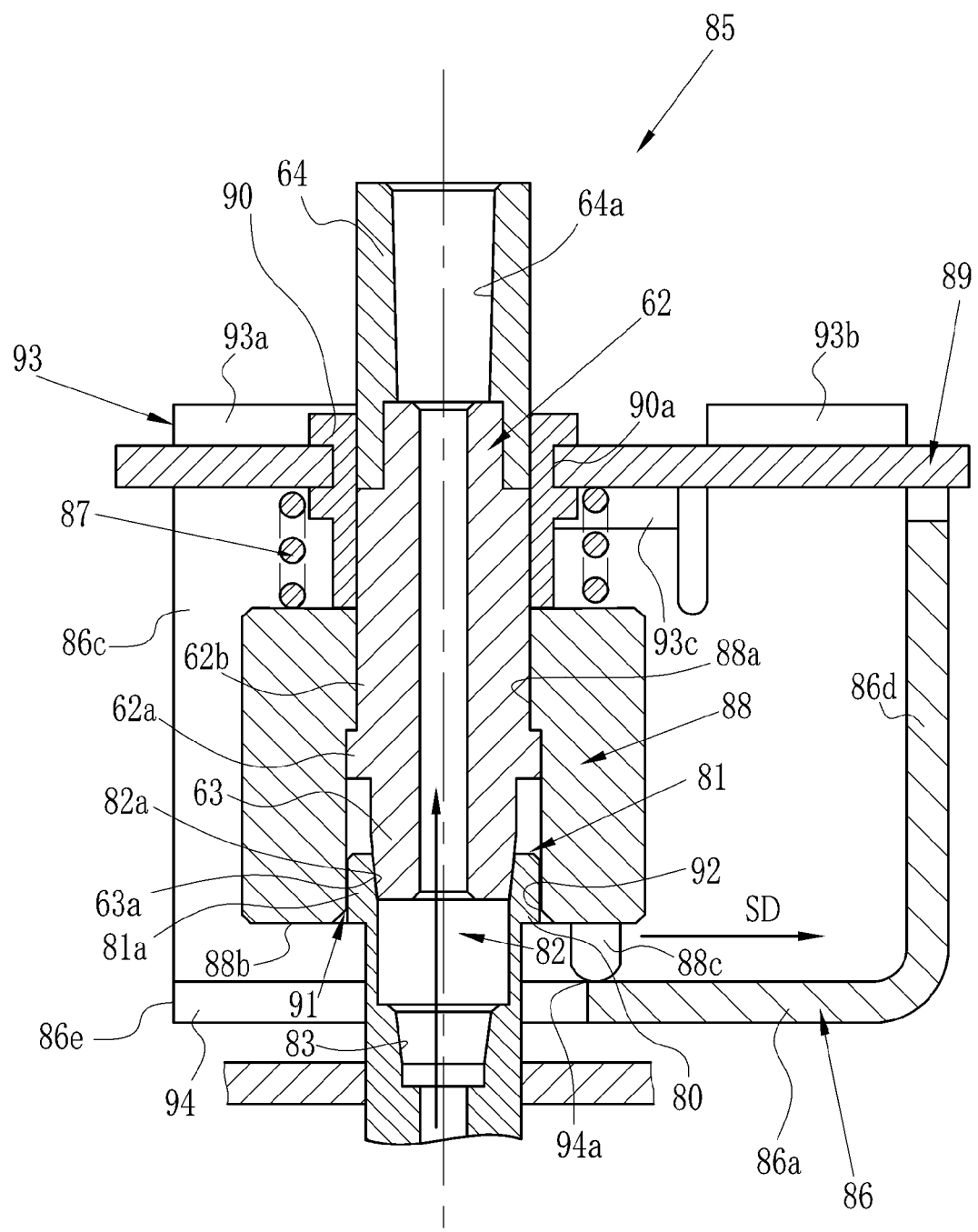
FIG. 17 is a cross section illustrating the same as FIG. 16 in the course of movement from a released position to a latched position.

In the above embodiment, the male thread 42b is disposed lower than the flange 42a. In FIGS. 11-13, a second preferred embodiment is illustrated, and includes a port device 71 or end sleeve, and a cleaning adapter 75 or second connector (fluid coupling). The port device 71 includes a flange 71a and a male thread 71b formed on the flange 71a. The first connector 52 of the above embodiment is repeated for use. Elements similar to those of the above embodiment are designated with identical reference numerals.

The port device 71 of the embodiment is disposed at the proximal flow opening of the light source connector 15 in the same manner as the first embodiment. The port device 71 includes the flange 71a, the male thread 71b, a guide projection 71c and an opening 72. The flange 71a continues from an upper surface, and projects from the sleeve portion 4. The male thread 71b is formed on the flange 71a. The guide projection 71c is disposed lower than the flange 71a. The opening 72 communicates with the fluid channel 41. The flange 71a is disposed at a predetermined interval from the guide projection 71c in the axial direction of the port device 71. The cleaning adapter 75 is helically engaged with the male thread 71b to be described later.

A female tapered surface 72a or tapered bore surface (first tapered portion) is defined inside the opening 72 and positioned at an upper end of the port device 71. The female tapered surface 72a tightly contacts the male tapered surface 63a of the cleaning adapter 75 to be described later. Also, a female Luer tapered surface 73 is defined in the opening 72 and positioned near to the fluid channel 41 lower than the female tapered surface 72a. The female Luer tapered surface 73 is adapted for engagement of a related apparatus in a shape of a male Luer tapered surface, and tapered at a taper angle different from that of the female tapered surface 72a.

The first connector 52 the same as the above embodiment is coupled to the port device 71. The engaging claws 54d of the first connector 52 are moved over the flange 71a and couple the first connector 52 to the port device 71 by engagement with the lower end 38 (rear end) of the flange 71a. In case the finger grip portions 54c are depressed, the arms 54b are moved to move the engaging claws 54d outwards in a radial direction of the connector housing 54. Thus, the engaging claws 54d are disengaged from the flange 71a to set the first connector 52 removable from the port device 71.

The first connector 52 and the cleaning adapter 75 are selectively couplable to the port device 71. The shape and coupling method are different between the first connector 52 and the cleaning adapter 75, so that no error occurs in the connection.

All of elements in the cleaning adapter 75 are metallic, inclusive of a connector housing 76 and the coupling sleeve 62. The cleaning adapter 75 is usable repeatedly as a reusable type the same as the first embodiment. The connector housing 76 is a barrel, and has a hole opening 77 directed to the light source connector 15. An inner surface 76a of the connector housing 76 has a smaller inner diameter than that of a guide surface 78 and a female thread 79 to be described later. The coupling sleeve 62 is axially fitted in the connector housing 76 in the axial direction. The small diameter portion 62b of the coupling sleeve 62 is engaged with the inner surface 76a of the connector housing 76 to attach the connector housing 76 to the coupling sleeve 62.

The male tapered surface 63a is disposed on an inner side and higher than a distal end surface 76b of the connector housing 76. The guide surface 78 is an inner surface of the hole opening 77 directed to the port device 71. The female thread 79 is disposed higher than the guide surface 78 and around the male tapered surface 63a. An inner diameter of the guide surface 78 is larger than that of the female thread 79 and slightly larger than an outer diameter of the guide projection 71c.

The female thread 79 is helically engaged with the male thread 71b of the port device 42. A size L2A of the guide surface 78 in the axial direction is longer than a distance L2B from an upper surface of the port device 71 to the guide projection 71c in the axial direction. At the beginning of threaded engagement between the male and female threads 71b and 79 after moving the male thread 71b to pass the guide surface 78, the guide projection 71c comes inside the guide surface 78. The guide surface 78 contacts an outer surface of the guide projection 71c to guide the port device 71. Thus, the male tapered surface 63a is axially aligned with the female tapered surface 72a. Further threaded engagement of the male thread 71b with the female thread 79 causes the male tapered surface 63a to contact the female tapered surface 72a.

The female thread 79 is helically engaged with the male thread 71b to latch the cleaning adapter 75 on the port device 71, and also presses the male tapered surface 63a to the female tapered surface 72a. In case the connector housing 76 is rotated in a direction to engage the female thread 79 helically with the male thread 71b, the connector housing 76 is moved toward the port device 71 according to threaded engagement of the male and female threads 71b and 79, to press the male tapered surface 63a to the female tapered surface 72a.

As described heretofore, all the elements in the cleaning adapter 75 are metallic, inclusive of the coupling sleeve 62, so that the cleaning adapter 75 can be used repeatedly with reusability. As the male tapered surface 63a is caused to press the female tapered surface 72a, the cleaning adapter 75 can be coupled to the port device 71 air-tightly or liquid-tightly in a sufficient manner.

In the above embodiments, the threads are engaged for fastening. In FIGS. 14-18, a third preferred embodiment is illustrated, and includes a cleaning adapter 85 or second connector (fluid coupling) and a port device 81 or end sleeve. The cleaning adapter 85 includes a shifting device 86 (fastening device) and a compression coil spring 87 (biasing device as pusher). The shifting device 86 moves relative to the coupling sleeve 62. The compression coil spring 87 biases the coupling sleeve 62 to the port device 81. The first connector 52 of the above embodiments is repeated for use. Elements similar to those of the above embodiments are designated with identical reference numerals.

The port device 81 for the endoscope of the present embodiment is disposed at the proximal flow opening of the light source connector 15 in a similar manner to the first embodiment. The port device 81 includes a flange 81a and an opening 82. The flange 81a continues from an upper surface and projects from the sleeve portion 4. The opening 82 communicates with the fluid channel 41. A female tapered surface 82a or tapered bore surface (first tapered portion) is defined inside the opening 82 and positioned at an upper end of the port device 81. The male tapered surface 63a of the cleaning adapter 85 to be described later tightly contacts the female tapered surface 82a. A female Luer tapered surface 83 is formed with the opening 82 and positioned near to the fluid channel 41 lower than the female tapered surface 82a. The female Luer tapered surface 83 is adapted for engagement of a related apparatus in a shape of a male Luer tapered surface, and tapered at a taper angle different from that of the female tapered surface 82a.

All elements in the cleaning adapter 85 are metallic, and include a connector housing 88, the coupling sleeve 62, a guide plate 89, a movable sleeve 90, the shifting device 86 and the compression coil spring 87. The cleaning adapter 85 is repeatedly usable in the manner of the above embodiments. The connector housing 88 is a barrel, and has a hole opening 91 directed to the light source connector 15. An inner surface 88a of the connector housing 88 has a smaller inner diameter than that of a guide surface 92. The coupling sleeve 62 is axially fitted in the connector housing 88. The small diameter portion 62b of the coupling sleeve 62 is engaged with the inner surface 88a of the connector housing 88 to attach the connector housing 88 to the coupling sleeve 62.

There is a distal end surface 88b of the connector housing 88. The male tapered surface 63a is disposed higher than the distal end surface 88b on an inner side. The male tapered surface 63a is so disposed that contact of the female tapered surface 82a of the port device 81 with the male tapered surface 63a positions a lower end 80 (rear end) of the flange 81a as high as the distal end surface 88b of the connector housing 88. The hole opening 91 in the connector housing 88 is directed to the port device 81. The guide surface 92 is formed inside the hole opening 91. An inner diameter of the guide surface 92 is larger than an outer diameter of the flange 81a. An engaging pin 88c or click pin is formed on the connector housing 88, and projects from the distal end surface 88b.

The guide plate 89 is associated with the small diameter portion 62b of the coupling sleeve 62 with the movable sleeve 90, and disposed higher than the connector housing 88 at a predetermined interval. The guide plate 89 is flat. A groove 90a is formed in the movable sleeve 90 in a circumferential direction. The guide plate 89 is received in the groove 90a and directed perpendicularly to the axis of the connector housing 88 and the coupling sleeve 62. The movable sleeve 90 and the guide plate 89 are slidable in the axial direction along the small diameter portion 62b.

The small diameter portion 62b is entered in the compression coil spring 87, which is disposed between the guide plate 89 and the connector housing 88. The compression coil spring 87 presses the connector housing 88 and the coupling sleeve 62 down toward the port device 81.

The shifting device 86 is in a bent form of a metal plate, and includes a lower plate 86a and side plates 86b, 86c and 86d, which are erect from the lower plate 86a in a box shape. The side plates 86b and 86c are opposed to one another, and also bent in directions to set their upper ends near to one another. A slide mechanism 93 is constituted by the side plates 86b and 86c and supported by the guide plate 89 in a slidable manner. The slide mechanism 93 includes slide arms 93a and 93b and a slide arm 93c. The slide arms 93a and 93b are received by an upper surface of the guide plate 89. The slide arm 93c is received by a lower surface of the guide plate 89. The shifting device 86 can be moved in a sliding direction SD perpendicular to (or transverse to) the axis of the connector housing 88 and the coupling sleeve 62 while guided by the guide plate 89. The side plate 86d is formed erectly from the lower plate 86a, and is disposed lower than the guide plate 89 to prevent interference of its upper end with the shifting device 86.

A plate edge 86e is located opposite to the side plate 86d in the shifting device 86. A cutout 94 is formed in the side plate 86c to open in the plate edge 86e, and aligned with the hole opening 91 of the connector housing 88. A size of the cutout 94 in a crosswise direction is larger than an outer diameter of the flange 81a. An inner edge 94a of the cutout 94 the farthest from the plate edge 86e is engageable with the lower end 80 of the flange 81a.

In case the shifting device 86 is pushed and slid toward the axis of the coupling sleeve 62 while guided by the guide plate 89, the inner edge 94a of the cutout 94 moves to the latched position of engagement with the lower end 80 of the flange 81a. In case the shifting device 86 is slid to set the inner edge 94a away from the axis of the coupling sleeve 62, the cutout 94 moves to the released position away from the lower end 80 of the flange 81a.

Engaging holes 95a and 95b or click holes are formed in the lower plate 86a, are arranged in the sliding direction SD of the shifting device 86, and receive the engaging pin 88c of the connector housing 88. Entry of the engaging pin 88c in the engaging hole 95a sets the shifting device 86 in a released position. Entry of the engaging pin 88c in the engaging hole 95b sets the shifting device 86 in a latched position.

To couple the cleaning adapter 85 to the port device 81, at first the shifting device 86 of the cleaning adapter 85 is set in the released position. See FIG. 16. The female tapered surface 82a of the port device 81 is set in tight contact with the male tapered surface 63a. The guide surface 92 of the connector housing 88 guides the flange 81a to align the male tapered surface 63a with the female tapered surface 82a axially.

Figure 18:
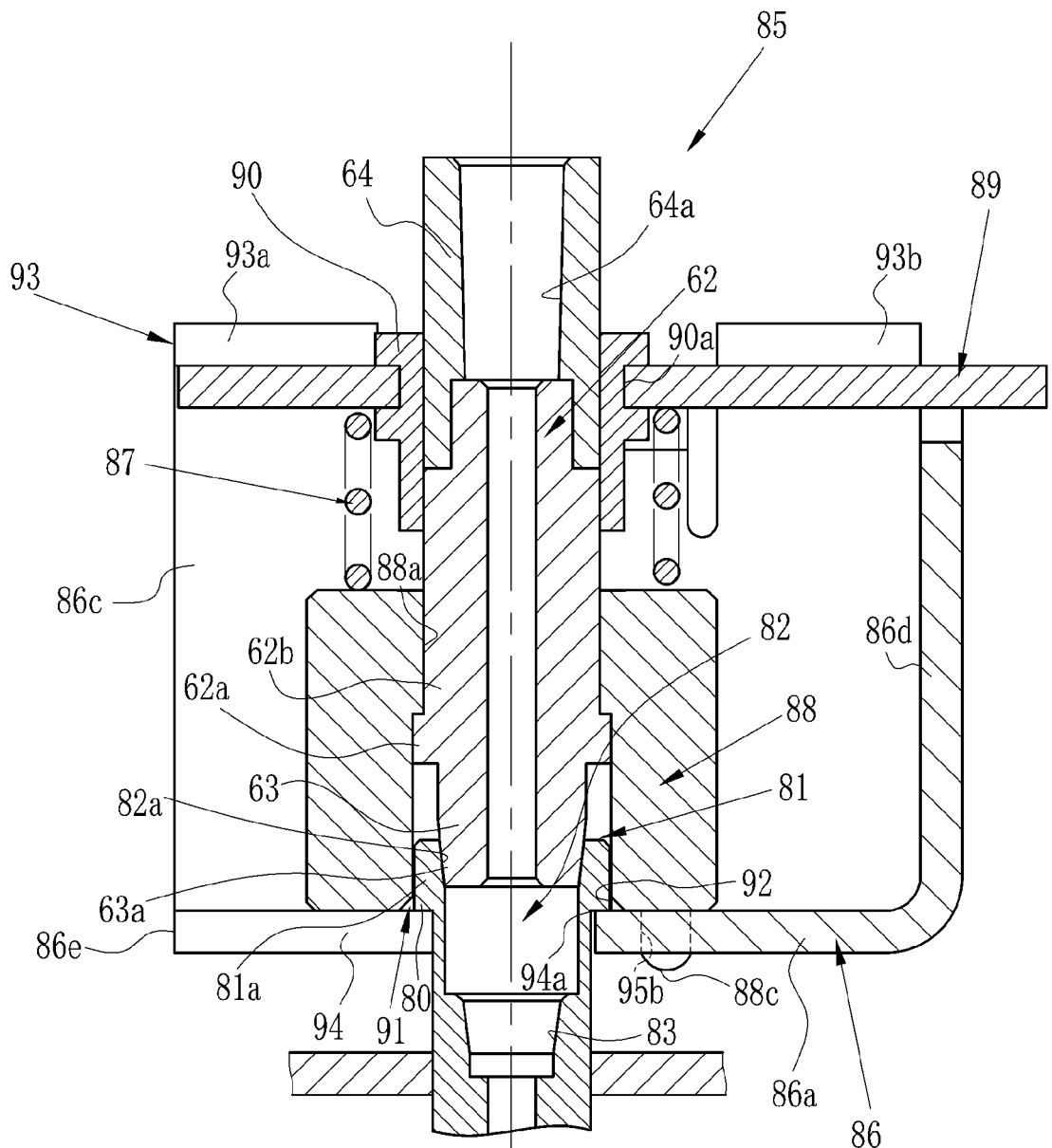
FIG. 18 is a cross section illustrating a fastened state of the cleaning adapter.
Figure 19:
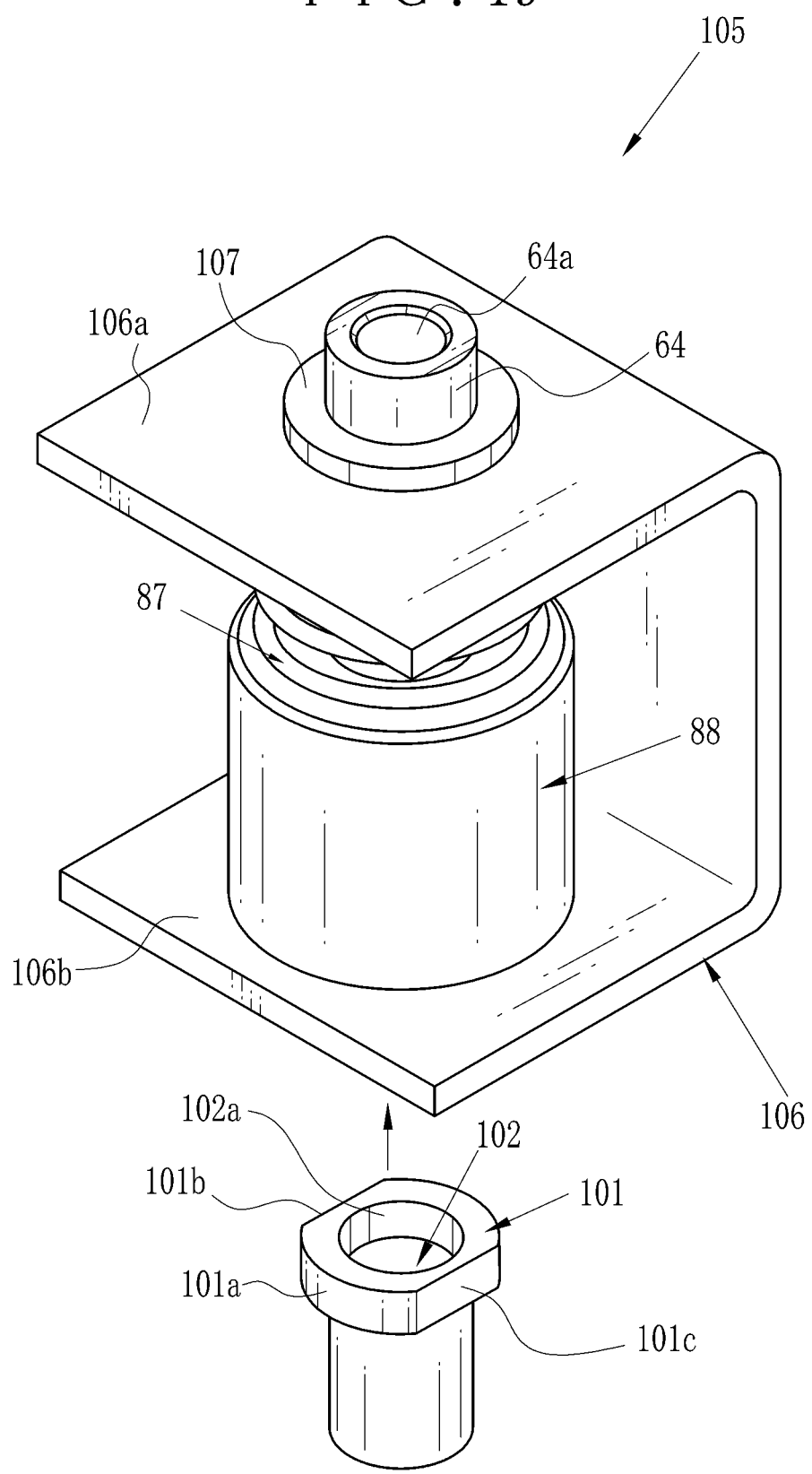
FIG. 19 is a perspective view illustrating a fourth preferred combination of a cleaning adapter and a port device.
Figure 20:
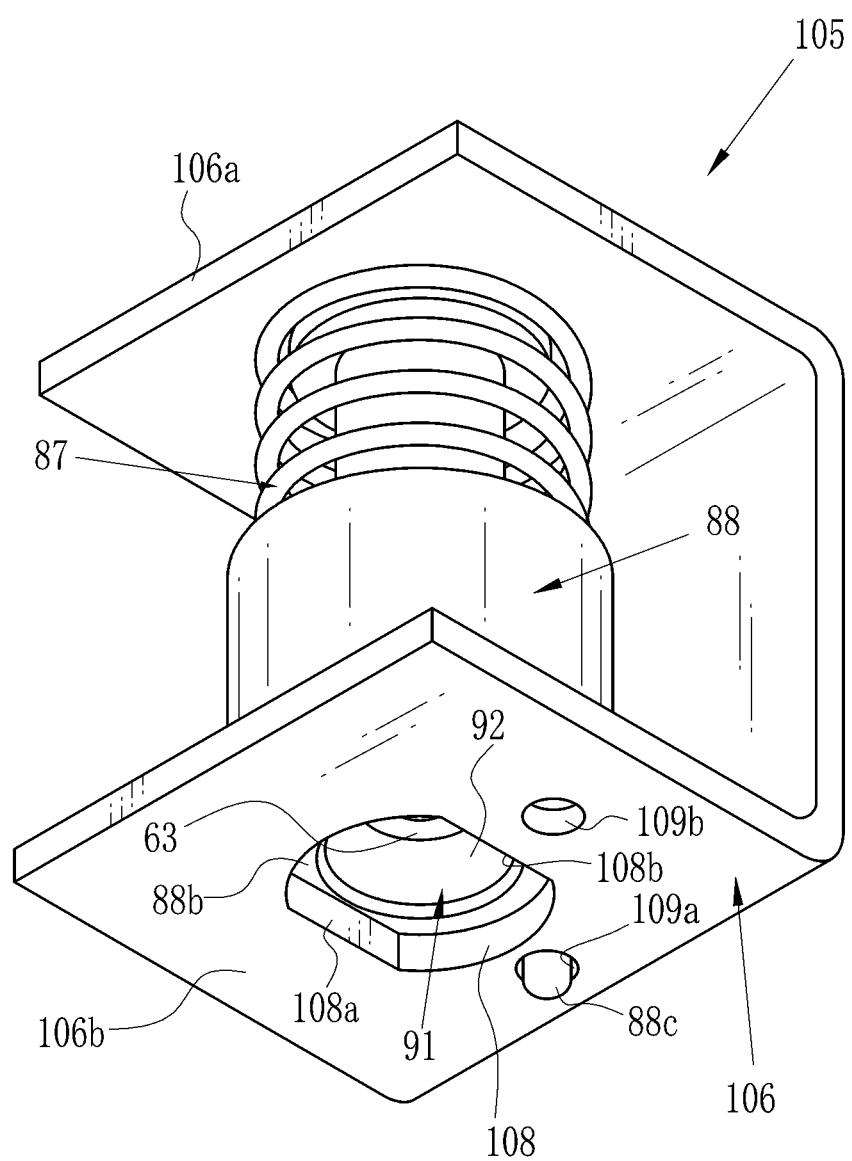
FIG. 20 is a bottom perspective view illustrating the cleaning adapter.
Figure 21:
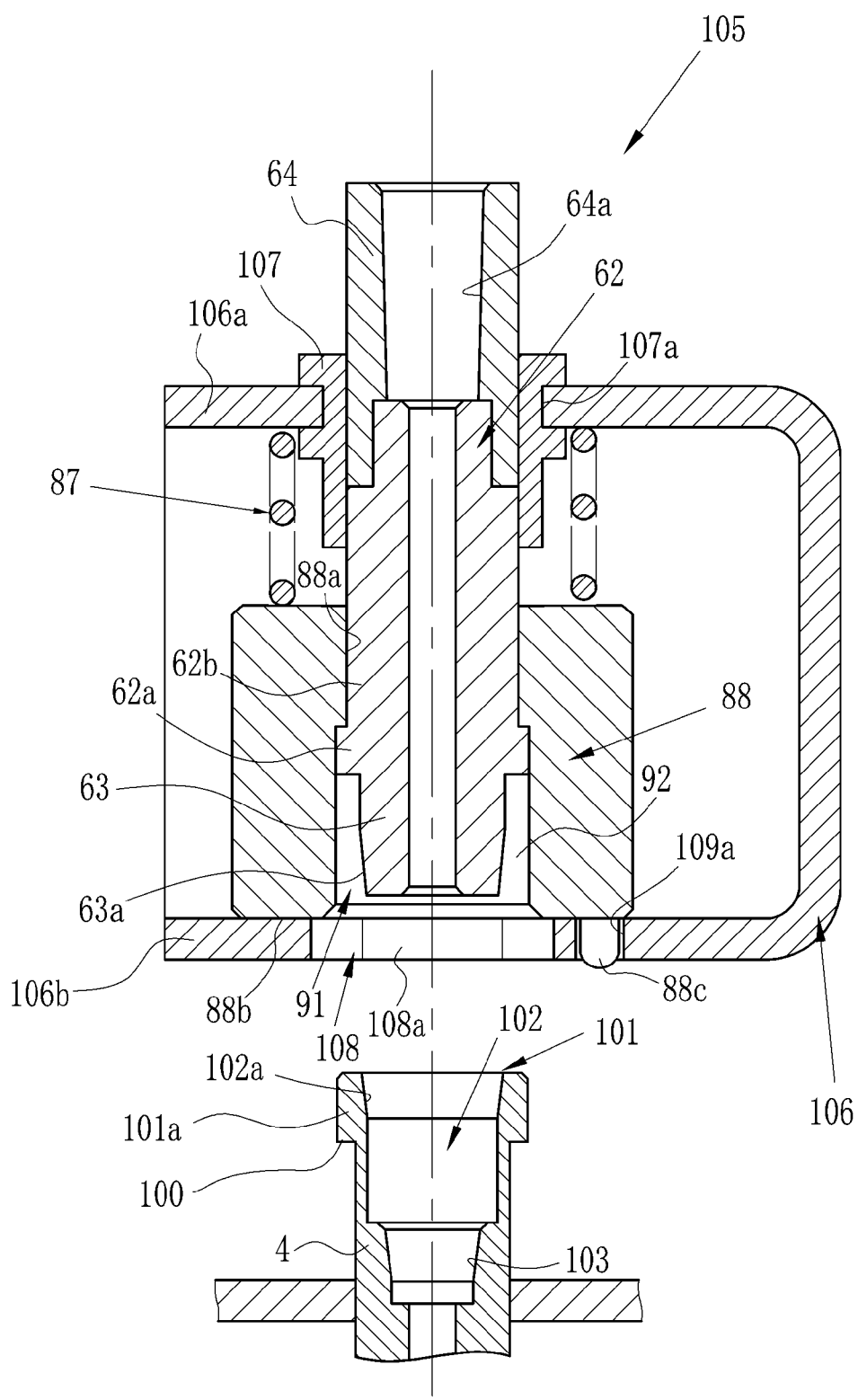
FIG. 21 is across section illustrating the cleaning adapter and the port device.

Furthermore, the port device 81 is pressed to an inner side of the connector housing 88 to compress the compression coil spring 87. The connector housing 88 moves up to disengage the engaging pin 88c from the engaging hole 95a. See FIG. 17. The shifting device 86 is slid toward the axis of the coupling sleeve 62 in the sliding direction SD. The engaging pin 88c is moved on an upper surface of the lower plate 86a and set at the engaging hole 95b. Then the compression coil spring 87 is released from the compression. The engaging pin 88c is entered in the engaging hole 95b, to set the shifting device 86 in the latched position. The inner edge 94a of the cutout 94 in the latched position is engaged with the lower end 80 of the flange 81a. The male tapered surface 63a tightly contacts the female tapered surface 82a to latch the port device 81. Thus, the cleaning adapter 85 is fastened on the port device 81 as illustrated in FIG. 18.

To remove the cleaning adapter 85 from the port device 81, the compression coil spring 87 is compressed by pushing the port device 81 to the inner side of the connector housing 88. The shifting device 86 is slid in a direction of moving the inner edge 94a of the cutout 94 away from the axis of the coupling sleeve 62, and moved from the latched position to the released position. In the released position, the edge portion of the cutout 94 is set away from the lower end 80 of the flange 81a. Thus, the cleaning adapter 85 is released from latching on the port device 81, and can be removed easily.

As described heretofore, all the elements in the cleaning adapter 85 are metallic, inclusive of the coupling sleeve 62, so that the cleaning adapter 85 can be used repeatedly with reusability. As the compression coil spring 87 causes the male tapered surface 63a to press the female tapered surface 82a, the cleaning adapter 85 can be coupled to the port device 81 air-tightly or liquid-tightly in a sufficient manner.

In the third embodiment, the cleaning adapter 85 has the shifting device 86 slidable between the released and latched positions. In FIGS. 19-22, another preferred cleaning adapter 105 or second connector (fluid coupling) includes a shifting device 106 (fastening device) rotatable between the released and latched positions. The first connector 52 of the first embodiment is repeated for use. Elements similar to those of the above embodiments are designated with identical reference numerals.

A port device 101 or end sleeve of the embodiment is disposed at the proximal flow opening of the light source connector 15 in the same manner as the first embodiment. The port device 101 includes a flange 101a and an opening 102. The flange 101a continues from an upper surface, and projects from the sleeve portion 4. The opening 102 communicates with the fluid channel 41. The flange 101a includes parallel walls 101b and 101c of edges parallel with one another. A female tapered surface 102a or tapered bore surface (first tapered portion) is defined in the opening 102 and positioned at an upper end of the port device 101. The male tapered surface 63a of the cleaning adapter 105 tightly contacts the female tapered surface 102a. Also, a female Luer tapered surface 103 is defined in the opening 102 and positioned near to the fluid channel 41 lower than the female tapered surface 102a. The female Luer tapered surface 103 is adapted for engagement of a related apparatus in a shape of a male Luer tapered surface, and tapered at a taper angle different from that of the female tapered surface 102a.

All elements in the cleaning adapter 105 are metallic, and include the connector housing 88, the coupling sleeve 62, the shifting device 106, a movable sleeve 107 and the compression coil spring 87. The cleaning adapter 105 is repeatedly usable in the manner of the above embodiments. In the connector housing 88, the male tapered surface 63a is so disposed that its tight contact with the female tapered surface 102a of the port device 101 locates a lower end 100 (rear end) of the flange 101a as high as the distal end surface 88b of the connector housing 88.

The shifting device 106 includes an upper plate 106a and a lower plate 106b opposed to one another in a U shape. The upper plate 106a of the shifting device 106 is disposed on the small diameter portion 62b of the coupling sleeve 62 with the movable sleeve 107 at a predetermined interval from the connector housing 88. A groove 107a is formed in the movable sleeve 107 and extends in a circumferential direction. The upper plate 106a of the shifting device 106 is received in the groove 107a and extends perpendicularly to the axial direction of the connector housing 88 and the coupling sleeve 62. The shifting device 106 and the movable sleeve 107 are rotatable about the axial direction with the small diameter portion 62b.

The lower plate 106b is disposed lower than the connector housing 88, and caused by the compression coil spring 87 to contact the distal end surface 88b of the connector housing 88. A through channel 108 is formed in the lower plate 106b and aligned with the hole opening 91 of the connector housing 88. The through channel 108 is slightly larger than a profile of the flange 101a. A pair of parallel walls 108a and 108b are defined by the through channel 108, and directed straight in compliance with the parallel walls 101b and 101c. The flange 101a is passable through the through channel 108 by aligning the parallel walls 101b and 101c with the parallel walls 108a and 108b of the through channel 108. However, the flange 101a cannot pass through the through channel 108 due to interference while the parallel walls 101b and 101c extend crosswise to the parallel walls 108a and 108b.

The shifting device 106 being rotated about the axis of the coupling sleeve 62, the edge of the through channel 108 moves to the latched position for engagement with the lower end 100 of the flange 101a. The shifting device 106 being rotated from the latched position at 90 degrees, the edge of the through channel 108 moves to a released position released from the lower end 100 of the flange 101a.

Engaging holes 109a and 109b or click holes are formed in the lower plate 106b, are arranged in a rotational direction (RD) of the shifting device 106, and receive the engaging pin 88c of the connector housing 88. Entry of the engaging pin 88c in the engaging hole 109a sets the shifting device 106 in a released position. Entry of the engaging pin 88c in the engaging hole 109b sets the shifting device 106 in a latched position.

To couple the cleaning adapter 105 to the port device 101, the parallel walls 101b and 101c of the flange 101a are aligned with the parallel walls 108a and 108b of the through channel 108. The flange 101a is passed and entered in the hole opening 91 of the connector housing 88. See FIG. 21. The female tapered surface 102a of the port device 101 is caused to contact the male tapered surface 63a tightly. The guide surface 92 of the connector housing 88 guides the flange 101a to align the male tapered surface 63a with the female tapered surface 102a axially.

Figure 22:
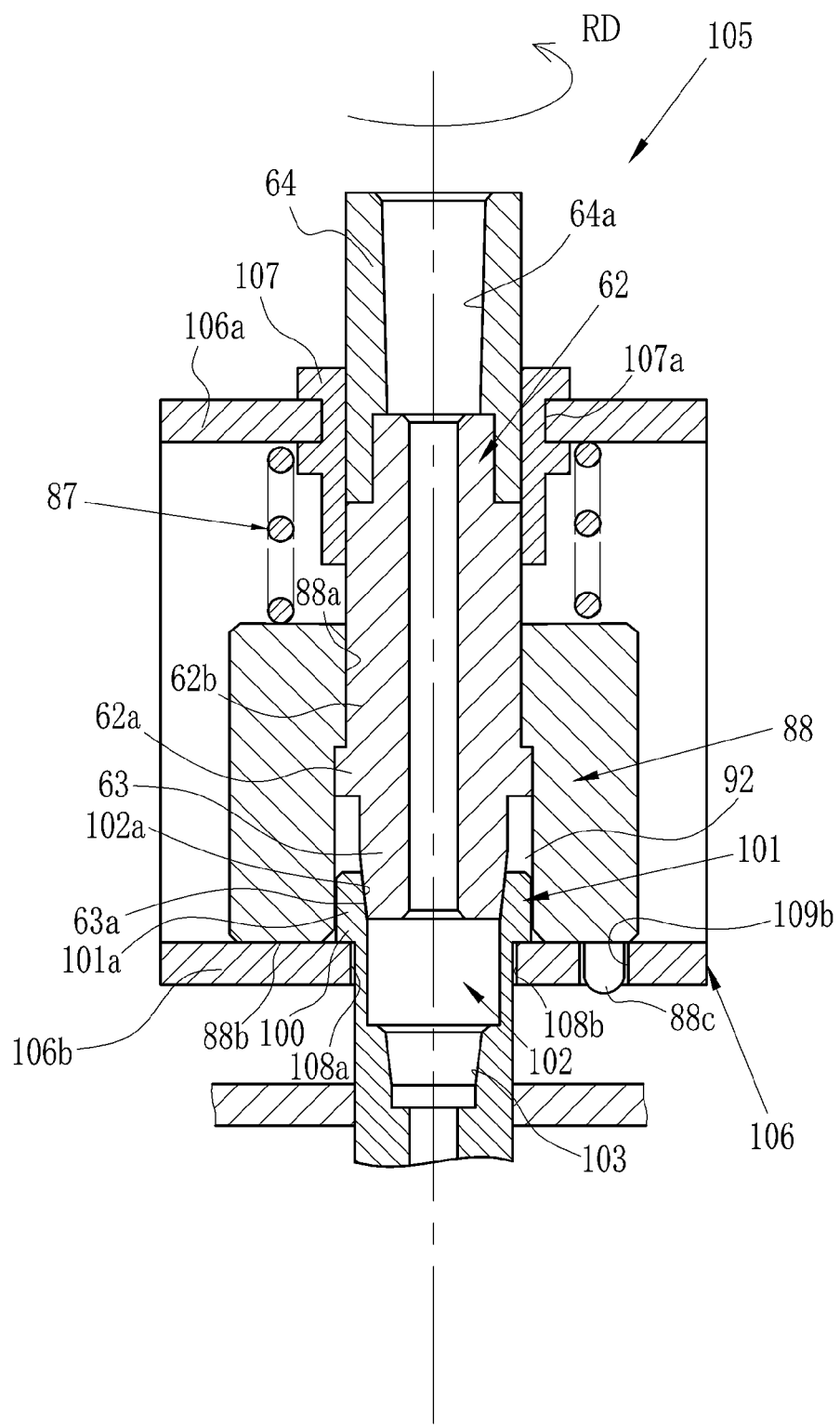
FIG. 22 is a cross section illustrating a fastened state of the cleaning adapter.

Furthermore, the port device 101 is pressed to an inner side of the connector housing 88 to compress the compression coil spring 87. The connector housing 88 moves up to disengage the engaging pin 88c from the engaging hole 109a. The shifting device 106 is rotated at 90 degrees about the axis of the coupling sleeve 62. The engaging pin 88c is moved on an upper surface of the lower plate 106b and set at the engaging hole 109b. Then the compression coil spring 87 is released from the compression. The engaging pin 88c is entered in the engaging hole 109b, to set the shifting device 106 in the latched position. The inner edge of the through channel 108 in the latched position is engaged with the lower end 100 of the flange 101a. The male tapered surface 63a tightly contacts the female tapered surface 102a to latch the port device 101. Thus, the cleaning adapter 85 is fastened on the port device 101 as illustrated in FIG. 22.

To remove the cleaning adapter 105 from the port device 101, the compression coil spring 87 is compressed by pushing the port device 101 to the inner side of the connector housing 88. The shifting device 106 is rotated at 90 degrees in a direction reverse to the initial rotational direction RD, and moved from the latched position to the released position. In the released position, the inner edge of the through channel 108 is set away from the lower end 100 of the flange 101a. Thus, the cleaning adapter 105 is released from latching on the port device 101, and can be removed easily.

Figure 23:
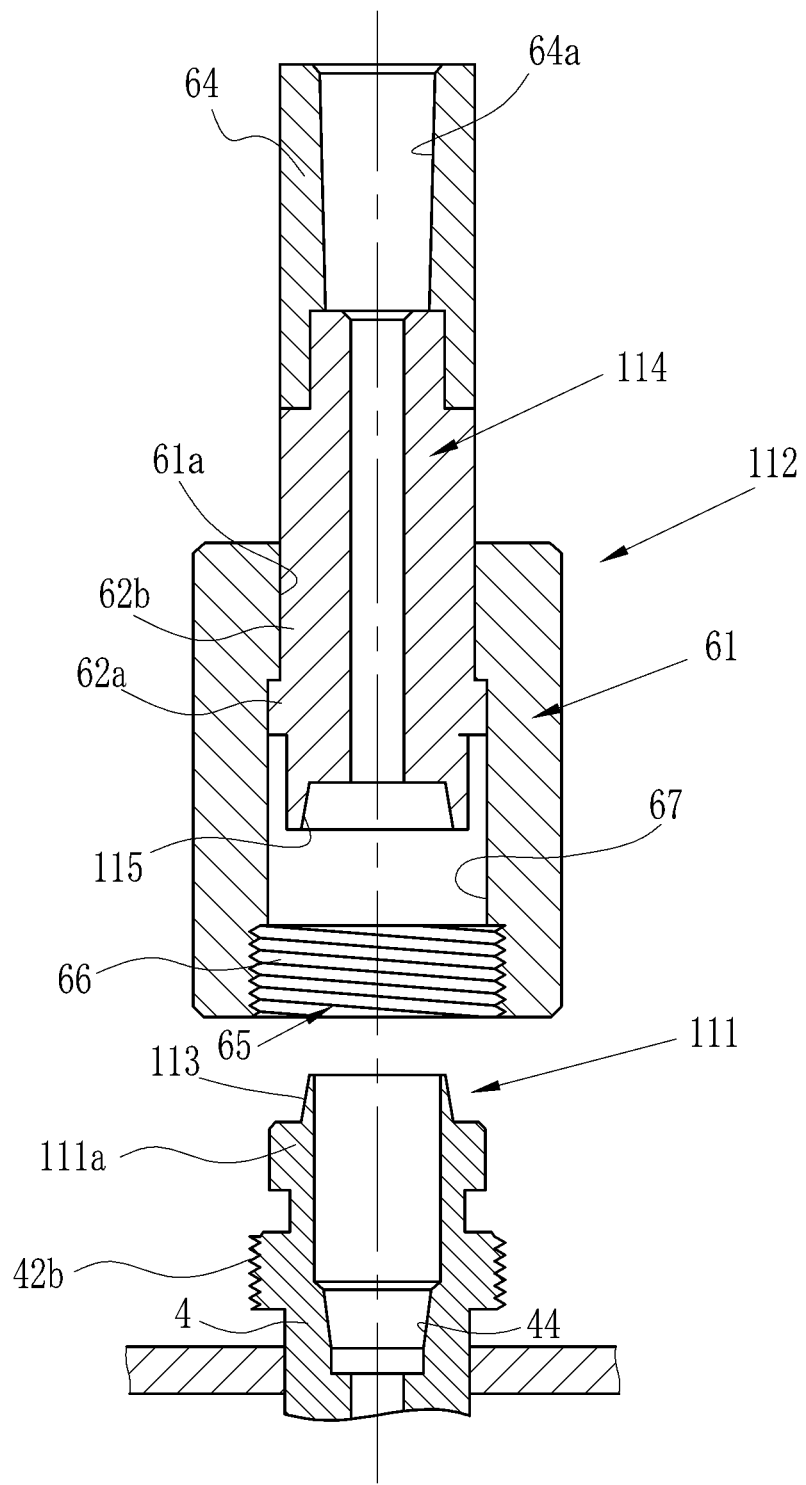
FIG. 23 is a cross section illustrating a variant combination of a cleaning adapter and a port device having tapered surfaces.

In FIG. 23, another preferred embodiment is illustrated, including a port device 111 or end sleeve, and a cleaning adapter 112 or second connector (fluid coupling). The port device 111 includes a flange 111a and a male tapered surface 113 or tapered sealing surface (first tapered portion) which projects from an upper end of the flange 111a. The cleaning adapter 112 includes a coupling sleeve 114 and a female tapered surface 115 or tapered bore surface (second tapered portion) at a lower end of the coupling sleeve 114. The coupling sleeve 114 is pushed to the port device 111 to keep the female tapered surface 115 in tight contact with the male tapered surface 113.

The feature of the invention is used with the fluid channel 41 and the port device in the endoscope 11 for fluid. However, the feature of the invention can be used with various channels in the field of the endoscope 11, such as a water jet channel for spraying fluid to an object in a body cavity through the tip device, a water supply channel for washing a viewing window of the tip device, an air supply channel for blowing liquid from the viewing window, and the like. A position of the port device is not limited to the light source connector 15, but can be the grip handle 13 or the like for communication with the fluid channel 41.

In the above embodiment, the related apparatus for connection of the second connector is the syringe for cleaning or tube cleaning apparatus. However, any one of known related apparatuses can be used in connection of the second connector. It is preferable to use metallic parts in the second connector, at least its second tapered portion on the connector side (male tapered portion 63), in consideration of reusability. Preferable examples of metals are stainless steel, titanium and the like having resistance to rust. Note that the second connector of the embodiments is a reusable type for repeated use. Note that the number of times in relation to the repeated use is 10 times or more.

The second connector (cleaning adapter 60, 75, 85, 105, 112) is constituted by the connector housing 61, 76, 88 and the coupling sleeve 62, 114 attached thereto. In the second connector (cleaning adapter), sizes, shapes, arrangement and the like of the connector housing 61, 76, 88 and the coupling sleeve 62, 114 are not limited to those of the embodiments.

The material of the parts in the second connector (cleaning adapter 60, 75, 85, 105, 112) may be metal and resin in combination, and also can be only resin. Desirable examples of the resin should be resins having sufficient durability and reusability.

In the above embodiments, a related apparatus connected with the first connector is the balloon control apparatus 47. However, a related apparatus connected by the first connector in the invention can be any one of various apparatuses for use in the imaging, diagnosis and manipulation for treatment, for example, an air supply apparatus, water supply apparatus, and fluid supply source for water jet. It is preferable to form the first connector 52 from resin at least partially in consideration of disposability. It is desirable to form all elements in the first connector from resin except for a sealing structure or seal packing.

In the above embodiment, the endoscope includes the image sensor for imaging. However, an endoscope of the invention can be a type in which an optical image guide device is used for imaging without using an image sensor.

According to a preferred mode embodiment of the invention, the second connector is adapted for connection to a related apparatus for cleaning or sterilization.

According to another preferred mode embodiment, the second connector is usable repeatedly.

According to one preferred mode embodiment, at least a portion of the first connector is plastic.

According to another preferred mode embodiment, the first connector is sterilized.

According to still another preferred mode embodiment, the first connector is adapted for connection of the fluid channel to a related apparatus.

According to another preferred mode embodiment, the first connector is disposable.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system, including an endoscope and first and second connectors, said endoscope having an elongated tube for entry in a body cavity for imaging, a fluid channel, formed inside said elongated tube, for transferring fluid, and a port device, disposed on a proximal end side of said elongated tube of said endoscope, for communicating with said fluid channel, said first and second connectors being selectively coupled with said port device, said endoscope system comprising: said port device including: a sleeve portion having an opening; a flange formed to project radially from an outer surface of said sleeve portion; a first tapered portion formed in said opening; said first connector including: a flow sleeve for entry in said opening; a sealing structure for sealing an outer surface of said flow sleeve entered in said opening; an engaging device for engagement with said flange; said second connector including: a coupling sleeve for entry in said opening; a second tapered portion, formed with said coupling sleeve, and tapered in compliance with said first tapered portion; a fastening device for fastening with said port device; a pusher for pressing said second tapered portion to said first tapered portion upon fastening of said fastening device with said port device, to seal said first and second tapered portions; wherein said port device further includes a third tapered portion that is formed in said opening between said first tapered portion and said fluid channel, and is tapered at a taper angle different from that of said first tapered portion.

2. An endoscope system as defined in claim 1, wherein said first tapered portion is a female tapered surface formed inside said port device, and said second tapered portion is a male tapered surface.

3. An endoscope system as defined in claim 2, further comprising a male thread formed with said port device;
wherein said fastening device includes a female thread for threaded engagement with said male thread for fastening.

4. An endoscope system as defined in claim 3, wherein said pusher is constituted by said female thread, and said second tapered portion is pressed to said first tapered portion according to threaded engagement of said female thread with said male thread.

5. An endoscope system as defined in claim 3, further comprising a guide surface, disposed around said second tapered portion, for guiding said port device, to position said first tapered portion on said second tapered portion.

6. An endoscope system as defined in claim 5, wherein said second connector includes a hole opening disposed so as to receive said port device;
said female thread is disposed between said hole opening and said guide surface, and said male thread is disposed between said flange and said fluid channel.

7. An endoscope system as defined in claim 5, wherein said second connector includes a hole opening disposed so as to receive said port device;
said guide surface is disposed between said hole opening and said female thread, and said male thread is disposed around said flange.

8. An endoscope system as defined in claim 7, further comprising a guide projection, formed around said port device between said flange and said fluid channel, for guiding by contacting said guide surface.

9. An endoscope system as defined in claim 3, wherein a size of said female thread in an axial direction is shorter than a distance from an upper end of said flange to said male thread in said axial direction.

10. An endoscope system as defined in claim 3, wherein a difference between a size of said female thread in an axial direction and a distance from an upper end of said flange to said male thread in said axial direction is equal to or more than 1 mm and equal to or less than 3 mm.

11. An endoscope system as defined in claim 2, wherein said pusher includes a biasing device for biasing said second tapered portion toward said port device;
said fastening device includes a shifting device movable between a latched position and a released position, said shifting device being engaged with a lower end of said flange, for fastening said second connector to said port device by latching said port device with said second tapered portion upon being set in said latched position, said shifting device unfastening said second connector from said port device by leaving from said lower end of said flange upon being set in said released position.

12. An endoscope system as defined in claim 11, wherein said shifting device is slidable between said released and latched positions relative to said second tapered portion and perpendicularly to an axial direction of said second connector.

13. An endoscope system as defined in claim 11, wherein said shifting device is rotatable between said released and latched positions about an axial direction of said second connector.

14. An endoscope system as defined in claim 2, wherein said third tapered portion includes a female Luer tapered surface, and;

said endoscope system further includes a male Luer tapered surface, disposed with a related apparatus for said endoscope, for engagement with said female Luer tapered surface.

15. An endoscope system as defined in claim 1, wherein at least a portion of said second connector having said second tapered portion is metallic.

\* \* \* \* \*